(12) United States Patent
Ikemoto et al.

(10) Patent No.: US 10,231,600 B2
(45) Date of Patent: Mar. 19, 2019

(54) IMAGE PROCESSING APPARATUS

(71) Applicant: HOYA CORPORATION, Tokyo (JP)

(72) Inventors: Yousuke Ikemoto, Tokyo (JP); Tadashi Minakuchi, Saitama (JP); Atsushi Komoro, Ibaraki (JP); Toshio Tachibana, Tokyo (JP); Noriko Ota, Saitama (JP)

(73) Assignee: HOYA CORPORATION, Tokyo (JP)

( * ) Notice: Subject to any disclaimer, the term of this patent is extended or adjusted under 35 U.S.C. 154(b) by 148 days.

(21) Appl. No.: 15/106,978

(22) PCT Filed: Feb. 8, 2016

(86) PCT No.: PCT/JP2016/053623
§ 371 (c)(1),
(2) Date: Jun. 21, 2016

(87) PCT Pub. No.: WO2016/136442
PCT Pub. Date: Sep. 1, 2016

(65) Prior Publication Data
US 2017/0112353 A1   Apr. 27, 2017

(30) Foreign Application Priority Data
Feb. 23, 2015 (JP) ................................. 2015-032714

(51) Int. Cl.
*A61B 1/04* (2006.01)
*A61B 1/00* (2006.01)
(Continued)

(52) U.S. Cl.
CPC ........ *A61B 1/00009* (2013.01); *A61B 1/0002* (2013.01); *A61B 1/0005* (2013.01);
(Continued)

(58) Field of Classification Search
CPC ..... A61B 1/00009; A61B 1/04; A61B 1/0005; A61B 5/1032; A61B 5/0084; A61B 1/00041
See application file for complete search history.

(56) References Cited

U.S. PATENT DOCUMENTS 9,430,833 B2   8/2016   Ikemoto
2005/0027166 A1   2/2005   Matsumoto et al.
(Continued)

FOREIGN PATENT DOCUMENTS

JP   2003-33327   2/2003
JP   2003-260027   9/2003
(Continued)

OTHER PUBLICATIONS

U.S. Appl. No. 15/106,955 to Yousuke Ikemoto et al., filed Jun. 21, 2016.
(Continued)

*Primary Examiner* — Rex R Holmes
(74) *Attorney, Agent, or Firm* — Greenblum & Bernstein, P.L.C.

(57) ABSTRACT

An image processing apparatus has a color image obtaining means configured obtain color image data representing a color image of biographic tissues, a lesion determining means configured to determine whether each pixel of the color image is of a lesion part based on the color image data, and a marking means configured to apply a mark indicating a position of the lesion part on the color image based on a result of determination, and the mark is configured such that the color image at a background of the mark can be seen.

18 Claims, 17 Drawing Sheets

(51) Int. Cl.
  *A61B 5/00* (2006.01)
  *A61B 5/103* (2006.01)
  *G06T 7/00* (2017.01)
  *G06T 7/11* (2017.01)

(52) U.S. Cl.
  CPC .......... *A61B 1/00041* (2013.01); *A61B 1/04* (2013.01); *A61B 5/0084* (2013.01); *A61B 5/1032* (2013.01); *G06T 7/0012* (2013.01); *G06T 7/11* (2017.01); *G06T 2207/10024* (2013.01); *G06T 2207/10068* (2013.01); *G06T 2207/30096* (2013.01)

(56) References Cited

U.S. PATENT DOCUMENTS

| | | | |
|---|---|---|---|
| 2005/0107691 A1 | 5/2005 | Zalis | |
| 2012/0319006 A1 | 12/2012 | Shida | |
| 2014/0320620 A1* | 10/2014 | Ikemoto | A61B 1/00009 348/71 |
| 2015/0181185 A1 | 6/2015 | Ikemoto et al. | |
| 2015/0193929 A1 | 7/2015 | Ikemoto | |
| 2015/0257635 A1 | 9/2015 | Kubo et al. | |

FOREIGN PATENT DOCUMENTS

| | | |
|---|---|---|
| JP | 2006-25802 | 2/2006 |
| JP | 2011-177419 | 9/2011 |
| JP | 2013-116353 A | 6/2013 |
| JP | 2014-18332 | 2/2014 |
| WO | 2014/084134 | 6/2014 |

OTHER PUBLICATIONS

International Preliminary Report on Patentability in PCT/JP2016/053623, with an English language translation dated Sep. 8, 2017.
Official Communication issued in European Patent Application No. 16728210.2, dated Oct. 15, 2018.

* cited by examiner

IMAGE PROCESSING APPARATUS

TECHNICAL FIELD

The present invention relates to an image processing apparatus configured to process an image of a biological tissue.

Generally, lesion parts of biological tissues exhibit a color different from that of normal parts. As the performance of color endoscopes has improved, it becomes possible the distinguish a lesion part of which color is only slightly different from the color of the normal parts. However, in order for an operator to accurately distinguish a lesion part from normal tissues by only a slight difference of the colors of the endoscopic image, the operator should have been trained by a skilled instructor for a long period. Further, it is not easy to distinguish the lesion parts by only a slight color difference for even a skilled operator, a careful operation is required.

It has been suggested, for example, in Japanese Patent Provisional Publication No. 2014-18332 (hereinafter, referred to as patent document 1), there is suggested an endoscope apparatus having a function of determining whether an object is a lesion part or not based on color information, and executing a color mapping process to change colors of pixels judged to be the lesion part in order that lesion parts can be distinguished easily, with respect to endoscopic image data photographed using white light.

SUMMARY OF THE INVENTION

In the marking image generated in Patent document 1, a portion suspected to be the lesion part is clearly distinguished by color. However, information of the image of the lesion part necessary for medical examination is deteriorated, and it is necessary to carefully compare the marking image with a normal observation image, which results in inconvenience that the medical examination is hard to be executed.

The present invention is made in view of the above circumstances and an object thereof is to provide an image processing apparatus capable of clearly indicating a portion suspected to be a lesion part with maintaining information of the image of the lesion part.

According to an embodiment of the present invention, there is provided an image processing apparatus, which has a color image obtaining means configured obtain color image data representing a color image of biographic tissues, a lesion determining means configured to determine whether each pixel of the color image is of a lesion part based on the color image data and a marking means configured to apply a mark indicating a position of the lesion part on the color image based on a result of determination, and the mark may be configured such that the color image at a background of the mark can be seen.

In the image processing apparatus described above, the lesion determining means may have a score table generating means configured to generate a score table including, as an element, a score representing severity degree of lesion of the biographical tissue per each pixel of the color image, and the marking means applies the mark indicative of a position and severity degree of the lesion part on the color image based on the score table.

According to this configuration, since information regarding the severity degree of a lesion can also be obtained from a mark applied on a color image, an advance diagnosis is possible based on objective data.

In the image processing apparatus described above, the marking means may be configured to set a mask which is a process target area within the color image, calculate a representative value of the score within the mask and apply the mark to the mask based on the representative value.

In the image processing apparatus described above, the marking means may be configured to set the mask having a predetermined initial size, calculate the representative value regarding the mask having the predetermined initial size, change the size of the mask in accordance with the representative value and apply the mark such that the mark inscribes in the mark of which size has been changed.

According to the above configuration, the severity degree of lesion is indicated by the size of the mark, the severity degree can be grasped intuitively from the image to which the mark is applied.

According to the above configuration, the initial size may be a minimum size of the mask.

According to the above configuration, the marking means may apply a corresponding number, that corresponds to the representative value, of the marks in the mask.

According to the above configuration, since the severity degree of the lesion is indicated by the density of the marks, the severity degree can be intuitively grasped from the image to which the marks are applied.

According to the above configuration, the marking means may apply the marks on the color image with causing the mask to scan within the color image.

According to the above configuration, the marking means may set the mask so as not to overlap another mask having been set.

According to this configuration, information of the mark having already been set is not lost, and accuracy of the information of the mark can be maintained.

According to the above configuration, the representative value may be one of an arithmetic mean value, a median value, a maximum frequency value, and a root-mean-square value.

According to the above configuration, the score table generating means may have a color space converting means configured to convert a color space of the color image data to another color space having one coordinate indicating intensity or brightness and two coordinates indicating color quality and a score calculating means configured to calculate the score per each pixel based on quality of color of each pixel of the color image data.

According to the above configuration, the score table generating means may further have a color enhancement means configured to execute a color enhancement processing to enhance contrast of the color quality at a boundary area within a pixel range value which is significant in the lesion part, and the score calculating means may calculate the score of each pixel based on the pixel values after the color enhancement processing has been executed.

According to the above configuration, the score calculating means may be configured to calculate the score of each pixel based on a distance to a reference point in a hue-saturation space or a chromaticity space.

According to the above configuration, the lesion part may be an inflammation part and the reference point may be a blood color.

According to the above configuration, the mark may he a symbolic character.

According to the above configuration, the mark may be a color having transparency.

According to the above configuration, the mark may be contour lines of the severity degree.

According to the above configuration, the color image may be an image taken by an electronic endoscope.

According to the embodiment of the present invention, since a mark through which a color image of the biological tissue can be seen is applied, and the shape or texture of the biological tissues can be grasped without referring to the color image before the mark is applied, an image diagnosis can be carried out more easily and accurately.

EMBODIMENTS FOR CARRYING OUT THE INVENTION

Figure 1:
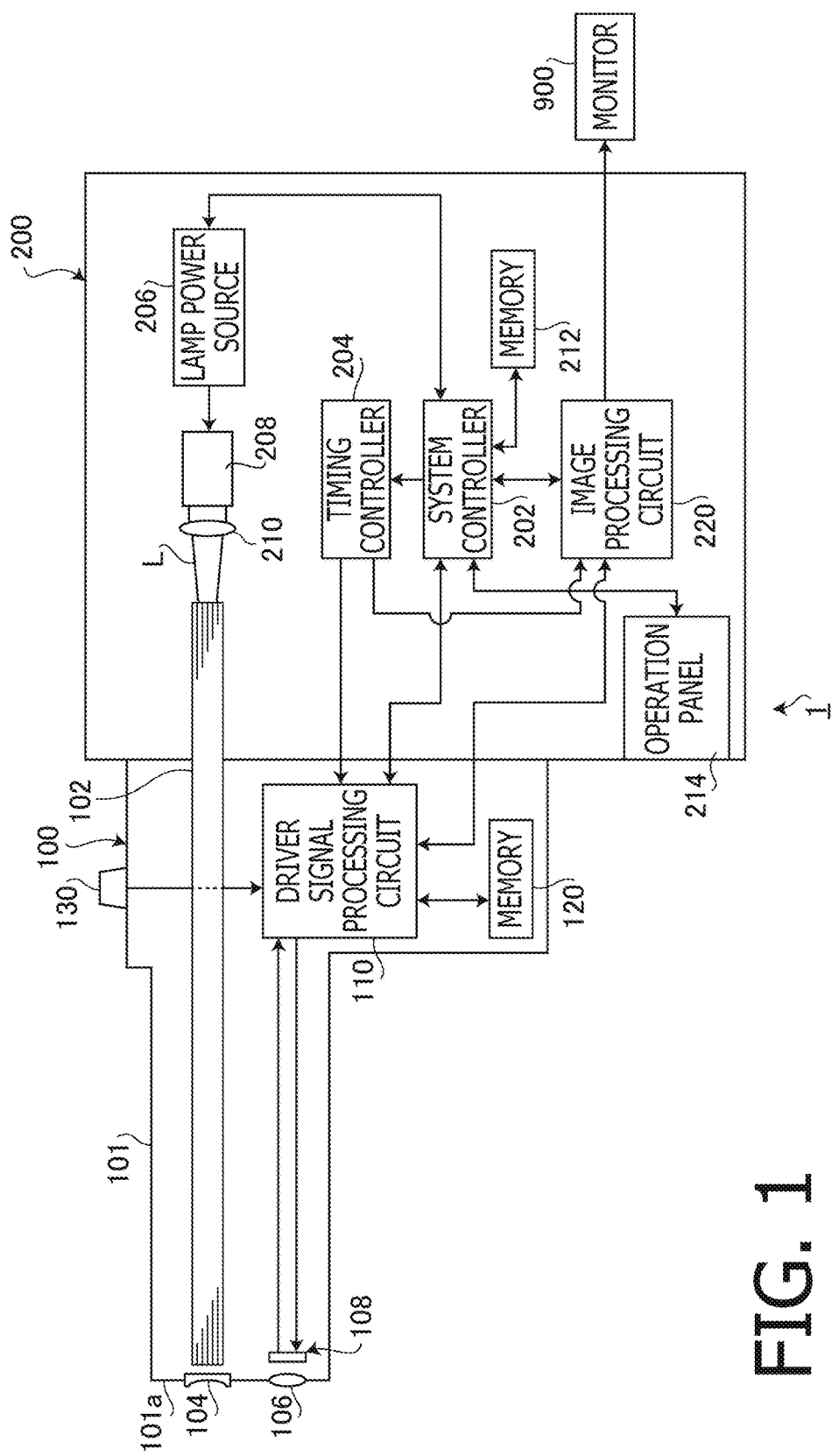
FIG. 1 is a block diagram schematically showing a configuration of an electronic endoscope apparatus according to an embodiment of the invention.

Hereinafter, referring to the drawings, embodiments of an image processing apparatus according to the present invention will be described. Incidentally, in the following description, an electronic endoscope system will be explained as one embodiment of the present invention.

<First Embodiment>

[Entire Configuration of Electronic Endoscope Apparatus 1]

FIG. 1 is a block diagram showing a configuration of an electronic endoscope apparatus 1 according to a first embodiment of the invention. As shown in FIG. 1, the electronic endoscope apparatus 1 is provided with an electronic scope 100, a processor 200 and a monitor 900.

The processor 200 is provided with a system controller 202 and a timing controller 204. The system controller 202 is configured to execute programs stored in a memory 212, and integrally control the electronic endoscope apparatus 1 entirely. The system controller 202 is connected to an operation panel 214. The system controller 202 changes operations of the electronic endoscope apparatus 1 and parameters for respective operations in accordance with instructions, which are input through the operation panel 214 by an operator. The timing controller 204 is configured to output synchronizing signals used to adjust operation timings of various parts to respective circuits of the electronic endoscope apparatus 1.

A lam 208 is actuated by a lamp power source igniter 206, and then, irradiates illuminating light L. The lamp 208 is, for example, a high-intensity lamp such as a xenon lam, a halogen lamp, a mercury lamp and a metal halide lamp, or an LED (light emitting diode). The illuminating light L is wideband light having a spectrum ranging mainly from a visible light region to an invisible infrared region (or, white light including at least visible light region).

The illuminating light L irradiated by the lamp 208 is converged on an incident surface of an LCB (light carrying bundle) 102 by a converging lens 210, and enters into the LCB 102.

The illuminating light L entered the LCB 102 propagates inside the LCB 102, emitted from a light emitting surface of the LCB 102 which is arranged at a distal end of the electronic scope 100, and is incident on an object through a distribution lens 104. Return light from the object, which is illuminated by the illuminating light L, is converged, by an objective lens 106, to focus an optical image on a light receiving surface of a solid state imaging element 108.

The solid state imaging element 108 is a single CCD (charge coupled device) image sensor in accordance with a complementary color checkered color difference line sequential system). The solid state imaging element 108 picks up an optical image focused on the light receiving surface, and outputs an analog photographing signal. Specifically, the solid state imaging element 108 accumulates the optical image focused on respective pixels of the light receiving surface as electric charges corresponding to light amounts, generates yellow (Ye), cyan (Cy), green (G) and magenta (Mg) color signals, and sequentially outputs scan lines obtained by adding and mixing generated color signals of each two pixels arranged next to each other in a vertical direction. Incidentally, the solid state imaging element 108 needs not be limited to a CCD image sensor, but can be replaced with CMOS (complementary metal oxide semiconductor) image sensor, or any other type of imaging device. Further, the solid state imaging element 108 may be one mounting a primary color system filter (e.g., a Bayer array filter).

Inside a connection part of the electronic scope 100, a driver signal processing circuit 110 is provided. The analog photographing signal including the scan lines described above is input to the driver signal processing circuit 110 from the solid state imaging element 108 at a field period. Incidentally, in the following description, a term "field" could be replaced with a term "frame." In the embodiment, the field period and a frame period are 1/60 second and 1/30 second, respectively. The driver signal processing circuit 110 applies a predetermined processing to the analog photographing signal transmitted from the solid state imaging element 108, and outputs the same to an image processing circuit 220 of the processor 200.

The driver signal processing circuit 110 is also configured to access a memory 120 and retrieves intrinsic information which is intrinsic to the electronic scope 100. The intrinsic information of the electronic scope 100 recorded in the memory 120 includes, for example, the number of pixels, a sensitivity, an operable field rate, a model number of the solid state imaging element 108. The driver signal processing circuit 100 transmits the intrinsic information retrieved from the memory 120 to the system controller 202.

The system controller 202 executes various operations based on the intrinsic information of the electronic scope 100 to generates control signals. The system controller 202 controls operations and timings of circuits in the processor 200, with use of the generated control signals, so that processes suitable to the electronic scope connected to the processor 200 will be executed.

The timing controller 204 generates a synchronizing signal in accordance with a timing control by the system controller 202. The driver signal processing circuit 110 controls and drives the solid state imaging element 108, in accordance with the synchronizing signal supplied from the timing controller 204, at a timing synchronously with the field rate of a video signal generated by the processor 200.

The image processing circuit 220 generates image data based on the photographing signal output by the electronic scope 100, under control of the system controller 202. The image processing circuit 220 generates a screen data for monitor display using the generated image data, converts the screen data to a video signal having a predetermined video format, and outputs the same. The video signal is input to the monitor 900, and a color image of the object is displayed on a display screen of the monitor 900.

Figure 2:
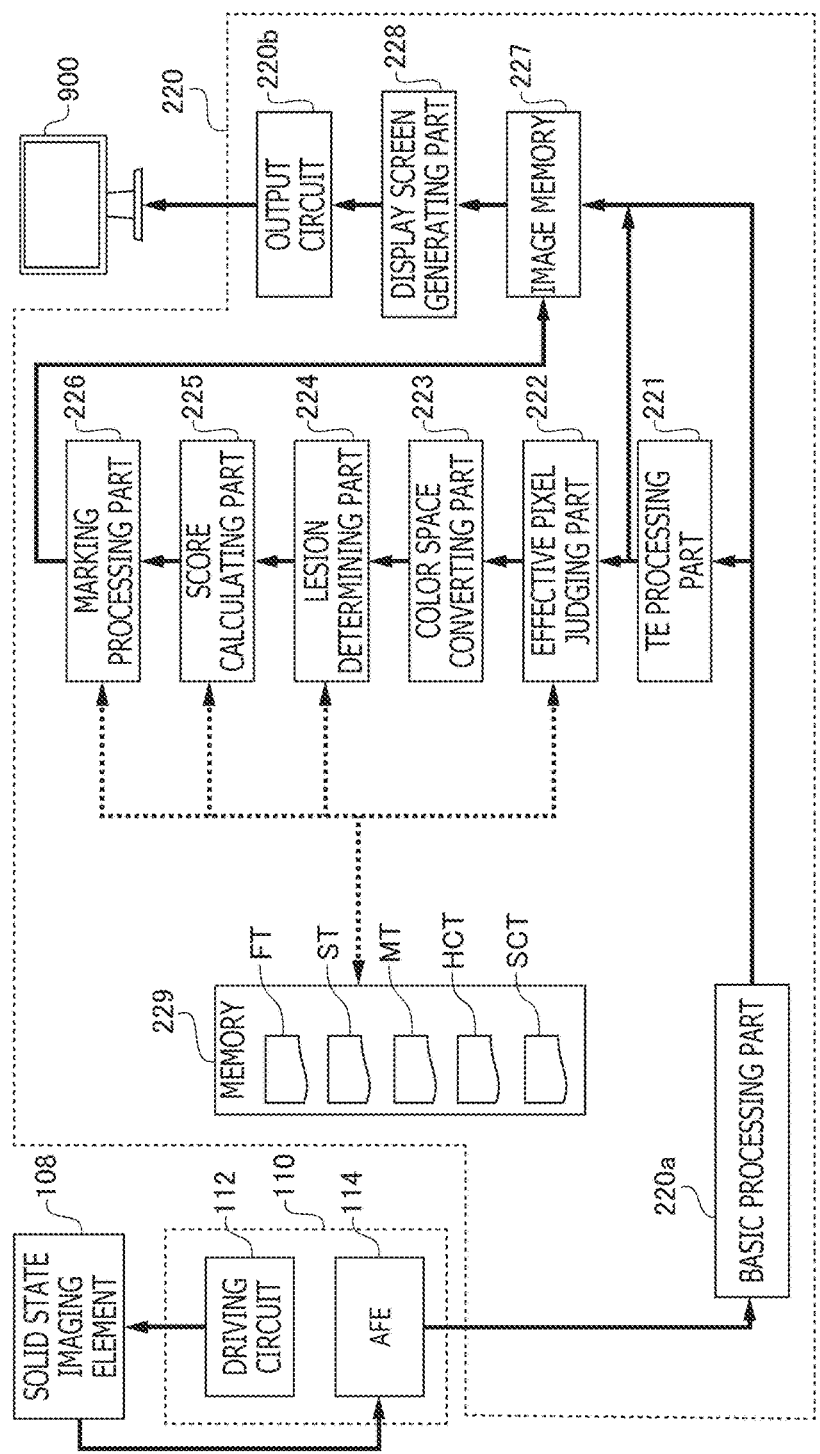
FIG. 2 is a block diagram schematically showing circuits regarding image processing of the electronic endoscope apparatus according to the embodiment of the invention.

FIG. 2 is a block diagram schematically showing a configuration of a circuit regarding image processing executed by the electronic endoscope apparatus 1.

The driver signal processing circuit 110 is provided with a driving circuit 112 and an AFE (analog front end) 114. The driving circuit 112 generates a driving signal of the solid state imaging element 108 in accordance with the synchronizing signal. The AFE 114 applies noise reduction, signal amplification, gain compensation and A/D (analog to digital) conversion with respect to the analog photographing signal, and outputs a digital image signal, and outputs a digital photographing signal. Incidentally, all or a part of processing executed by the AFE 114 according to the embodiment may be executed by the solid state imaging element 108 or the image processing circuit 220.

The image processing circuit 220 is provided with a basic processing part 220a, an output circuit 220b, a TE (tone enhancement) processing part 221 an effective pixel judging part 222, a color space converting part 223, a lesion determining part 224, a score calculating part 225, a marking processing part 226, an image memory 227, a display screen generating part 228, a memory 229 and a reliability evaluating part 230. Processing executed by each part of the image processing circuit 220 will be described later.

Figure 3:
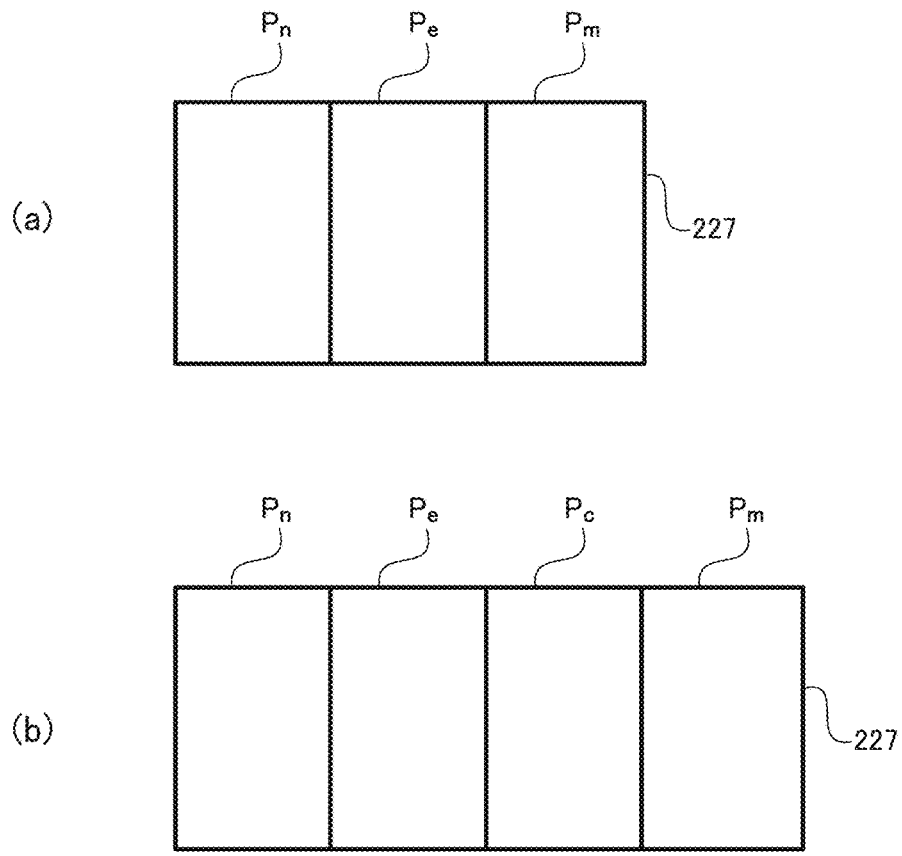
FIG. 3 is a drawing schematically showing a configuration of storage areas of an image memory.

FIG. 3(a) schematically shows a configuration of storage areas allocated in the image memory 227. In the image memory 227 according to the embodiment, three storage areas Pn, Pe and Pm are allocated. The storage area Pn is an area which stores normal observation image data N (i.e., image data representing a normal observation image NP) which is generated by the basic processing part 220a. Incidentally, in the storage area Pn, two pieces or more of normal observation image data N subsequently generated can be stored. The storage area Pe is an area which stores tone-enhanced image data E (i.e., image data representing a tone-enhanced image EP) generated by a TE processing part 221. The storage area Pin is an area which stores marking image data M (i.e., image data representing a marking image MP) generated by the marking processing part 226.

As shown in FIG. 2, a flag table FT, a score table ST, a mask table MT, a hue correlation value table HCT and a saturation correlation value table SCT are stored in the memory 229. The flag table FT, and the score table ST are numeral value table having flags F (x, y) and scores Sc (s, y) representing analysis results regarding pixels (x, y) of the normal observation image data N, respectively. Specifically, the flags F (x, y) are parameters indicating presence/absence of lesions of tissues photographed on the corresponding pixels (x, y), the scores Sc (x, y) are parameters representing the severity degree of the lesions. The hue correlation value table HCT, the saturation correlation value table SCT and the mask table MT will be described later.

[Basic Processing S1]

Figure 4:
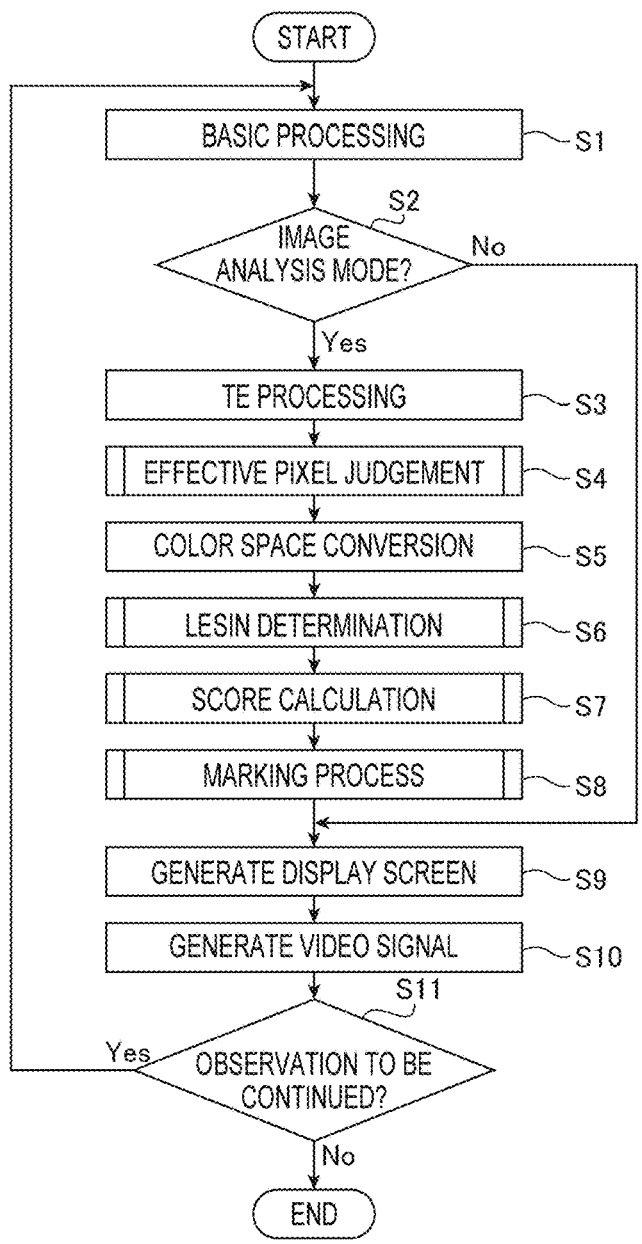
FIG. 4 is a flowchart illustrating a procedure of a process executed by an image processing circuit.

Next, processes executed by the image processing circuit 220 will be described. FIG. 4 is a flowchart illustrating procedures of the process executed by the image processing circuit 220. With respect to a digital signal output by the APE 114, general signal processing (i.e., a basic processing S1) is applied by the basic processing part 220a, and normal observation image data N is generated.

The basic processing S1 includes a process of converting the digital photographing signal output by the AFE 114 to a intensity signal Y, and color difference signals Cb and Cr, a primary color separation process of separating primary colors R, G and B from the intensity signal Y, and color difference signals Cb and Cr, a clamp process of removing offset components, a defective pixel correction process of correcting a pixel value of a defective pixel with use of pixel values of surrounding pixels, a de-mosaic process (i.e., an interpolation process) of converting photographing data (i.e., RAW data) consisting of monochromatic pixel values to image data having full-color pixel values, a linear matrix process of correcting a spectral characteristic of the imaging element with use of a color matrix, a white balance process of compensating for spectral property of the illuminating light, and a contour correction process of compensating for deterioration of a spatial frequency characteristic.

Incidentally, all or part of the processes executed by the basic processing part 220a in the embodiment may be executed by the driver signal processing circuit 110 or the solid state imaging element 108.

The normal observation image data N generated by the basic processing part 220a is transmitted to the TE processing part 221 and the scene judging part 230, and further stored in the storage area Pn of the image memory 227.

[Operation Mode Judging Process S2]

Next, whether an operation mode is set to an image analysis mode (S2) is judged. The image analysis mode according to the embodiment of the invention is an operation mode in which color information is analyzed with respect each pixel of the image data, it is judged whether each pixel is a pixel photographing a lesion part (hereinafter, referred to as a lesion pixel) based on the result of analysis of the color information and a predetermined judging criteria, and the lesion pixels are displayed in a discriminated manner. Kinds of lesions to be judged can be selected depending on inspection contents. In an example described below, pixels of color range which is intrinsic to observation images of inflammation (e.g., reddening inflammation including selling or easy bleeding) of inflammatory bowel disease (IBD) are displayed in a discriminated manner.

It is noted that the electronic endoscope apparatus 1 according to the embodiment is configured to operate in either of two operation modes: an image analysis mode; and a normal observation mode. The operation mode is switched by a user operation to an operation part 130 of the electronic scope 100 or the operation panel 214 of the processor 200. When the operation mode is set to the normal observation mode (S2: NO), process proceeds to S9.

[TE (Tone Enhancement) Process S3]

Figure 5:
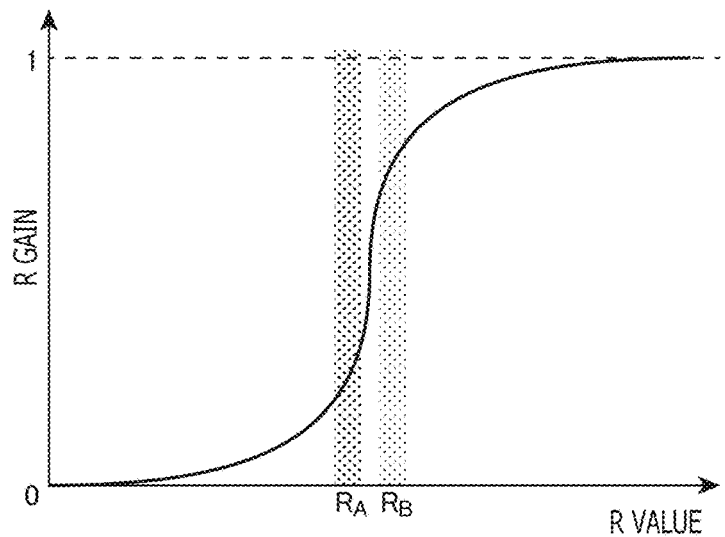
FIG. 5 shows an example of a gain curve used in a TE process.

When the image analysis mode is selected (S2: YES), the TE process S3, which is to be executed by the TE processing part 221, is executed subsequently. The TE process S3 is a process of increasing an effective resolution by performing gain adjustment to give a non-linear gain to each of primary color signals R, G and B of the normal observation image data N, thereby substantially expanding a dynamic range in the vicinity of a characteristic color range (in particular, a boundary portion thereof) of the lesion subject to judgment. Specifically, in the TE process S3, a process of applying the non-linear gain as shown in FIG. 5 to each of primary color signals R, G and B to obtain primary color signals R', G' and B' (i.e., tone-enhanced image data E) is executed. For example, a gain curve shown in FIG. 5 is shaped such that an inclination of the curve is steep from a boundary range $R_A$, which is a characteristic color range of an ulcer, to a boundary region $R_B$, which is a characteristic color range of inflammation. By applying the gain in accordance with such a gain curve, a substantial dynamic range-of the primary color signal R' (i.e., a signal obtained by applying the TE process S3 to the primary color signal R) from the boundary range $R_A$ to the boundary range $R_B$ can be expanded, thereby further precise threshold value judgment being enabled.

Incidentally, by the TE process S3, the hue changes such that the inflammatory part becomes reddish, the ulcer part becomes whitish and the normal part becomes greenish. Therefore, when the tone-enhanced image data E, which is generated in the TE process S3, is displayed on the monitor 900, lesion part (e.g., the inflammatory part or the ulcer part) can easily be visually recognized in comparison with a case where the normal observation image data N before the TE process S3 is applied is displayed. It is noted that the TE process S3 above is an example of a color enhancement process applicable to the present invention. Instead of the TE process S3, another type of color enhancement process capable of enhancing color quality, specifically, the hue or contrast of saturation (or chromaticity), may be employed.

[Effective Pixel Judging Process S4]

After the TE process S3 has completed, the effective pixel judging part 222 applies the effective pixel judging process S4 to the tone-enhanced image data E. It is noted that, the TE process S3 is omitted and the effective pixel judging process S4 may be applied to the normal observation image data N.

Figure 6:
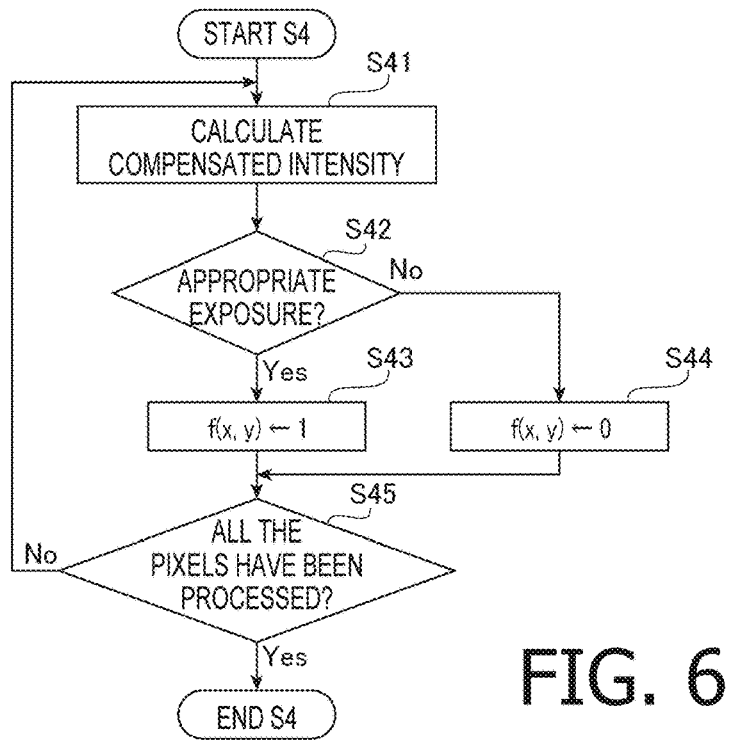
FIG. 6 is a flowchart illustrating a procedure of an effective pixel judging process.

FIG. 6 is a flowchart illustrating a procedure of the effective pixel judging process S4. The effective pixel judging process S4 is a process of judging whether pixel values are suitable for image analysis, and is sequentially executed to all the pixels (x, y) constituting the image data. In the effective pixel judging process S4, firstly, for each pixel (x, y), based on the primary color signals R'(x, y), G'(x, y) and B'(x, y) of the tone-enhanced image data E, corrected intensity int(x, y) is calculated with use of formula 1 below.

$$\text{int}(x, y) = 0.3 * R'(x, y) + 0.59 * G'(x, y) + 0.11 * B'(x, y) \quad \text{[Formula 1]}$$

Incidentally, values of the corrected intensity int(x, y) as calculated are used in a following appropriate exposure judging process S42. Further, as known from formula 1, the corrected intensity int(x, y) is not a simple average of the primary color signals R'(x, y), G'(x, y) and B'(x, y), but is obtained as a weighted average based on relative spectral sensitivity characteristic of human beings (e.g., the operator).

Next, for each pixel (x, y), the appropriate exposure judging process S42 is executed, in which whether the exposure level is appropriate to image analysis is judged based on the corrected intensity int(x, y) of the tone-enhanced image data E calculated in process S41 and the primary color signals R'(x, y), G'(x, y) and B'(x, y). In the appropriate exposure judging process S42, the exposure is determined to be the appropriate exposure (S42: YES) when at least one of (or both of the following two conditions (i.e., formulae 2 and 3) is satisfied. Incidentally, formula 2 defines an upper limit value of the corrected intensity int(x, y) (the entire light amount), while formula 3 defines a lower limit value of each of the primary color signals R'(x, y), G'(x, y) and B'(x, y).

$$\text{int}(x, y) < 235 \quad \text{[Formula 2]}$$

$$\text{Max}\{R'(x, y), G'(x, y), B'(x, y)\} > 20 \quad \text{[Formula 3]}$$

If, for the pixel (x, y), it is determined that formula 2 or formula 3 (or both formulae 2 and 3) is satisfied and the exposure is appropriate (S42: YES), the effective pixel judging part 222 rewrites the value of a flag F(x, y), which corresponds to the pixel (x, y), of the flag table FT stored in the memory 229 with value "1" (S43).

It is noted that the flag F (x, y) has a flag value of one of 0-2. Each flag value is defined below.

0: invalid pixel data
1: normal or unjudged (pixel data is valid)
2: lesion (inflammation)

In the appropriate exposure judging process S42, if none of the formulae 2 and 3 is satisfied (or one of the formulae 2 and 3 is not satisfied), and the exposure is determined to be inappropriate (S42: NO), the effective pixel judging part 222 rewrites the value of the flag F(x, y) of the flag table FT with "0" (S44).

In process S45, it is judged whether the process has been completed for all the pixels (x, y). Unless all the pixels (x, y) have been processed, the above processes S41-S45 are repeated.

[Color Space Converting Process S5]

When the effective pixel judging process S4 has completed, the color space converting part 223 applies a color space converting process S5 to the tone-enhanced image data E. The color space converting process S5 is a process of converting pixel values of an RGB space defined by RGB three primary colors to pixel values of HIS (Hue-Saturation-Intensity) space defined by three elements of hue, saturation and intensity. Specifically, in the color space converting process S5, the primary color signals R'(x, y), G'(x, y) and B'(x, y) of each pixel (x, y) of the TE image data E is converted to hue H(x, y), saturation S(x, y) and intensity I(s, y).

Further, data of under or over exposure pixels (x, y) has low accuracy and lowers reliability degree of the analysis results. Therefore, the color space converting process S5 is applied only to the pixels (x, y) of which the value of the flag F(x, y) is set to be one (1) (i.e., the pixels (x, y) judged to be appropriately exposed in the effective pixel judging process S4).

Decision image data J{H(x, y), S(x, y), I(x, y)} having hue H(x, y), saturation S(x, y) and intensity I(x, y) of each pixel (x, y), which are generated by the color space converting part 223, is transmitted to the lesion determining part 224.

[Lesion Determining Process S6]

After completion of the color space conversion process S5, the lesion determining part 224 executes a lesion judging process S6 using the decision image data J, the lesion determining process S6 is a process applied to each pixel (x, y) of the endoscope image, in which process a condition of the biological tissue photographed by the pixel is determined (i.e., it is judged whether the biological tissue is in the inflammatory condition) depending on whether the decision image data J is plotted on which of areas α or β (see FIG. 8; described later) in an HS space (i.e., Hue-Saturation space). It is noted that the HS space is, similar to the a chromaticity space, a space representing quality of colors (i.e., components excluding brightness/intensity). For example, when the image analysis is performed on another color space such as a CIE 1976 L*a*b* color space, lesion determination by the lesion determining part 224 is executed on the chromaticity space (e.g., an a*b*space).

Figure 7:
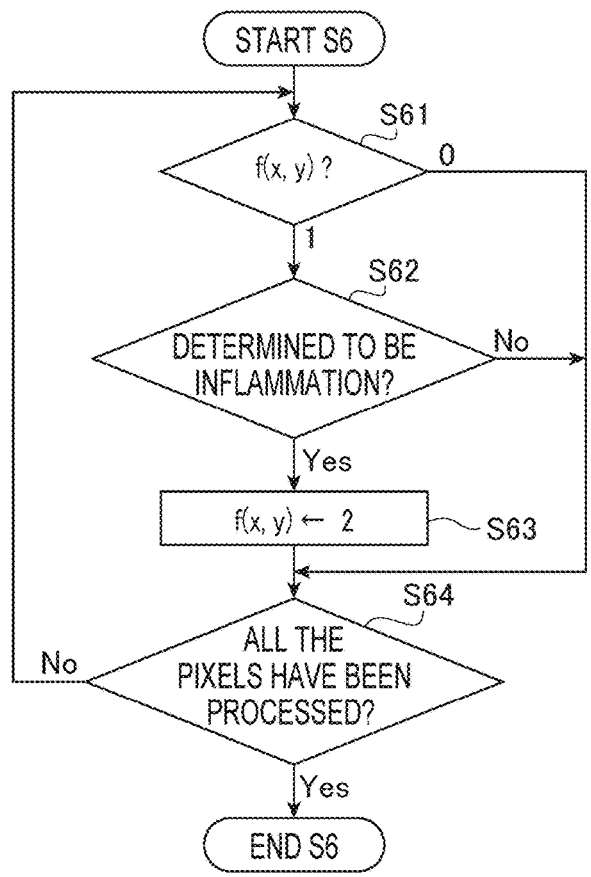
FIG. 7 is a flowchart illustrating a procedure of a lesion judging process.

FIG. 7 is a flowchart illustrating a procedure of the lesion determining process S6. The lesion determining process S6 is executed for all the pixels (x, y) constituting the image data, sequentially. In the lesion determining process S6, firstly, it is determined whether data of each pixel (x, y) is valid, referring to the flag table FT (S61). When the value of the flag F(x, y) is "1" (i.e., the pixel data is valid), an inflammation determining process S62 is executed. When the value of the flag F(x, y) is "0" (i.e., the pixel data is invalid), control proceeds to process S64 without executing the inflammation determining process S62.

Figure 8:
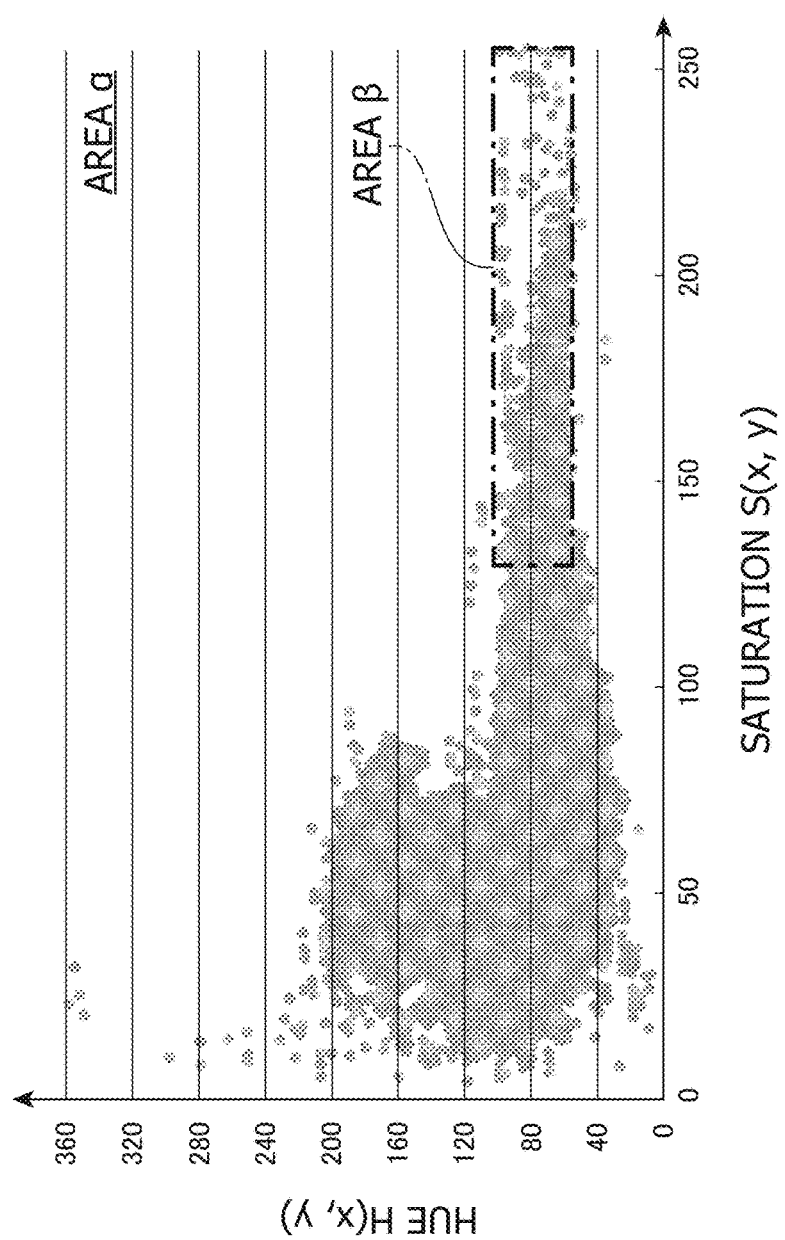
FIG. 8 is a scatter diagram in which pixel values of biological tissues are plotted in an HS coordinate space.

The inflammation determining process S62 executed in the lesion determining process S6 will be described. FIG. 8 is a scatter diagram which shows that decision image data J obtained from the endoscope image data of a plurality of inflammatory bowel disease patients is plotted in an HS coordinate space.

The scatter diagram shown in FIG. 8 is classified into area β which is located on a lower right portion and encircled by broken lines, and area α which is an area other than area β. According to the research of the inventors of the present invention, it has become clear that most of the portions determined as inflammatory portions by doctors who are skilled in endoscopic diagnosis of the inflammatory bowel disease are plotted in area β, while most of the portions determined as non-inflammatory portions by the doctors skilled in endoscopic diagnosis of the inflammatory bowel disease are plotted in area α. From the above, the condition of the biological tissue (i.e., presence/absence of the inflammation) can be judged with sufficient accuracy based on the two pieces of information of the hue (shade of color) and saturation (vividness of color) of the endoscopic observation image photographing biological tissues.

In the inflammation determining process S62, it is determined whether decision image data J{H(x, y), S(x, y)} of each pixel (x, y) is to be plotted in area β shown in FIG. 8. Specifically, the decision image data J{H(x, y), S(x, y)} is plotted in area β when both formulae 4 and 5 below are satisfied. When the decision image data J{H(x, y), S(x, y)} does not satisfy at least one of formulae 4 and 5, the decision image data J{H(x, y), S(x, y)} is plotted in area α (i.e., it is determined that the pixels are not those of the inflammatory portions). Incidentally, $\delta_{S1}$, $\delta_{H1}$ and $\delta_{H2}$ are compensation values which can be set by the operator, and by the settings of these compensation values, strictness of decision (i.e., sensitivity) can be appropriately adjusted.

$$130+\delta_{S1} \leq S(x, y) \qquad \text{[Formula 4]}$$

$$60+\delta_{H1} \leq H(x, y) \leq 100+\delta_{H2} \qquad \text{[Formula 5]}$$

When the decision image data J{H(x, y), S(x, y)} of a pixel (x, y) is plotted in area β (S62: YES), the value of the flag F(x, y) corresponding to the pixel (x, y) is rewritten with "2" (i.e., inflammation) (S63), and control proceeds to process S64. When the decision image data J{H(x, y), S(x, y)} of a pixel (x, y) is not plotted in area β (S62: NO), the flag F(x, y) is not rewritten, and control proceeds to process S64.

In process S64, it is judged whether all the pixels (x, y) have been processed. Until all the pixels (x, y) are processed, above processes S61-S64 are repeated.

[Score Calculating Process S7]

After the lesion determining process S6 has completed, a score calculating process S7 is executed. The score calculating process S7 is a process of calculating a score Sc(x, y) representing an evaluation value of severity degree of the lesion part based on the pixel values of the decision image data J. The score calculating process S7 is executed sequentially for all the pixels (x, y) constituting the image data. Incidentally, an algorithm of the score calculation explained below is only an example, and the present invention can be applied to displayed screens of scores calculated in various algorithms, respectively.

[Principle of Score Calculation]

Here, a principle of score calculation according to the embodiment will be described briefly. It is known that the more a symptom of an inflammatory part progresses, the closer the color of the inflammatory part becomes the color of blood as superficial normal mucous membranes will be fallen out. Therefore, degree of correlation between the color of the inflammatory part and the color of the blood (i.e., correlation value CV, which will be described later) serves as a good index representing the severity degree of the inflammatory part. According to the present embodiment, the correlation value CV(x, y) representing the relative correlation between the decision image data J{H(x, y), S(x, y)} of each pixel (x, y) and a color of the blood (i.e., hue and saturation) is calculated, which is used as the score Sc(x, y) representing the severity of the inflammatory part.

[Lesion Part Judgment S71]

Figure 9:
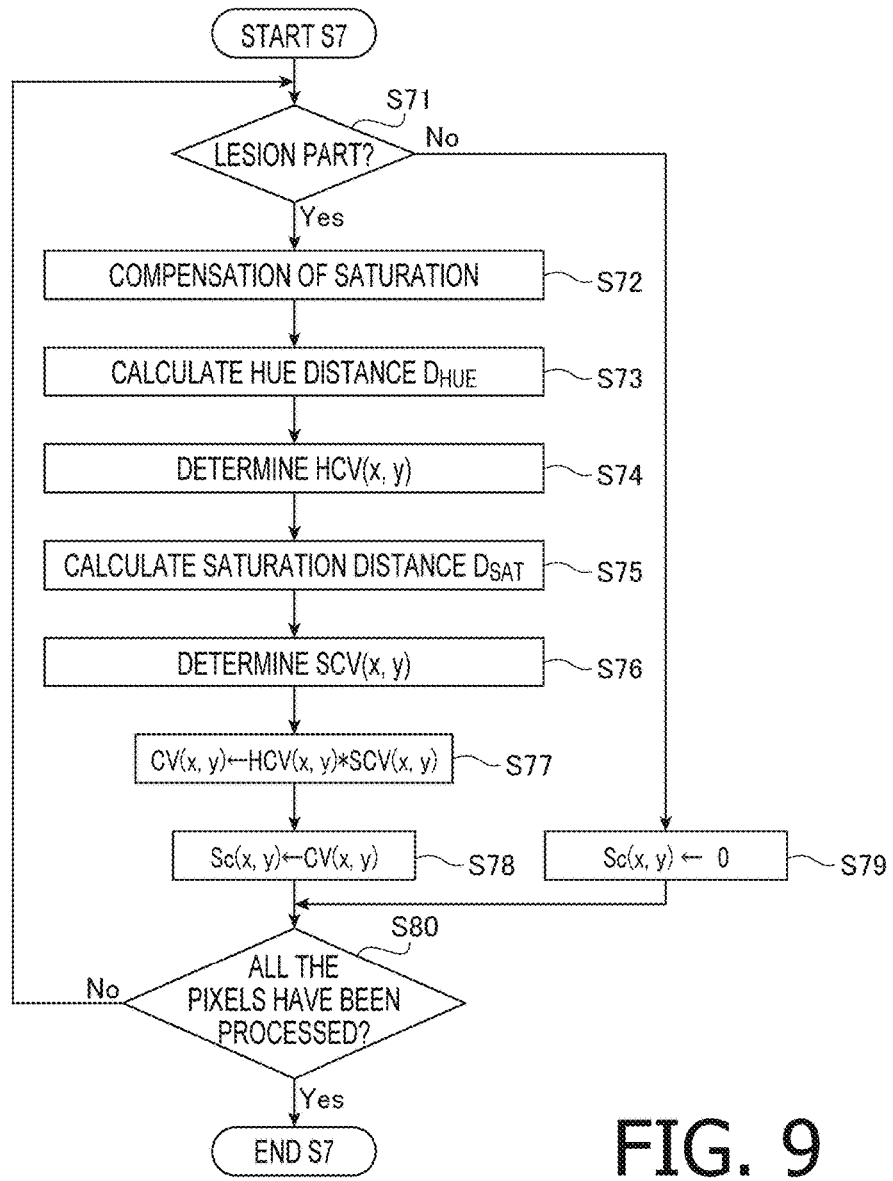
FIG. 9 is a flowchart illustrating a procedure of a score calculating process.

FIG. 9 is a flowchart illustrating a procedure of the score calculation process S7. In the score calculation process S7, the flag table FT is firstly retrieved, and it is judged whether the value of the flag F(x, y) corresponding to the pixel (x, y) is "2" (i.e., inflammation) (S71).

When the value of the flag F(x, y) is "2" (inflammation), namely, when the pixel (x, y) is the lesion pixel (S71: YES), process proceeds to S72. When the pixel (x, y) is not the lesion pixel (S71: NO), process proceeds to S79.

[Compensation of Saturation: S72]

It is known that saturation of blood or biological tissue including blood depends on its intensity. Specifically, saturation thereof is lower as the intensity is higher. In S72, variation of saturation S(x, y) due to intensity I(x, y) of the decision image data J(x, y) is compensated using formula 6 which is developed by the present inventors. By applying this compensation, it is possible to make precision of score calculation higher.

$$\begin{bmatrix} I_{corr.}(x, y) \\ S_{corr.}(x, y) \end{bmatrix} = \begin{bmatrix} \cos\theta & -\sin\theta \\ \sin\theta & \cos\theta \end{bmatrix} \begin{bmatrix} I(x, y) \\ S(x, y) \end{bmatrix} + \begin{bmatrix} I_{ref} \\ S_{ref} \end{bmatrix}$$ [Formula 6]

where, $I_{corr.}(x, y)$: luminance of the decision image data J after compensation;

$S_{corr.}(x, y)$: saturation of the decision image data J after compensation;

$I_{ref}$: luminance of blood sample data serving as a reference value; and $\theta$: an angle providing with a correlation index ($\cos \theta$) between the saturation and the luminance of the blood sample.

It is noted that the correlation index (measured value) is −0.86, and accordingly, $\theta$=149.32 (degree) is used.

(Calculation of Hue Distance $D_{HUE}$: S73)

Next, using formula 7, a hue distance $D_{HUE}(x, y)$ is calculated (S73). The hue distance $D_{HUE}$ is a relative value of the hue of the decision image data J(x, y) using the hue $H_{ref}$ of the blood sample data as reference.

$$D_{HUE}(x, y)=H(x, y)-H_{ref}$$ [Formula 7]

[Determination of Hue Correlation Value HVC: S74]

Figure 10:
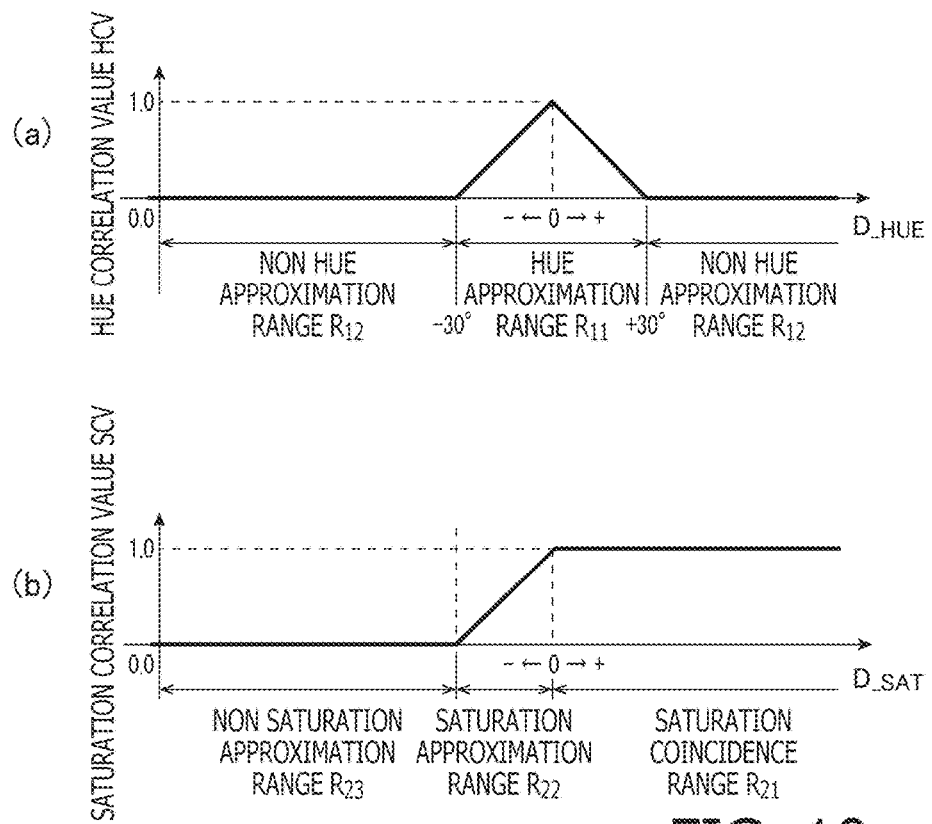
FIG. 10 shows graphs showing relationships between a hue distance, a saturation distance and correlation values.

Next, a hue correlation value HVC(x, y) is determined (S74) based on the hue distance $D_{HUE}(x, y)$. The hue correlation value HCV(x, y) is a parameter having strong correlation with severity degree of an inflammation part. FIG. 10(a) is a graph showing a relationship between the hue distance $D_{HUE}$ and the hue correlation value HCV. The hue distance $D_{HUE}$ exhibits a strong correlation with the severity degree of the inflammation part within a range of ±30° (hereinafter, referred to as a "hue approximation range $R_{11}$"), while exhibits little correlation in other ranges. Therefore, the hue correlation value HCV(x, y) of the present embodiment is set to a minimum value of 0.0 in a non-hue approximation range $R_{12}$, and set to linearly increase as the hue distance $D_{HUE}(x, y)$ approaches 0° within the hue approximation ranges $R_{11}$. Further, the hue correlation value HCV(x, y) is normalized such that the minimum and maximum values of the hue correlation values HCV(x, y) are 0.0 and 1.0, respectively.

The relationship between the hue distance $D_{HUE}$ and the hue correlation value HCV shown in FIG. 10(a) is stored in the memory 229 in form of a hue correlation value table HCT. By referring to the hue correlation value table HCT, a hue correlation value HCV(x, y) corresponding to a hue distance $D_{HUE}(x, y)$ can be obtained.

[Calculation of Saturation Distance: S75]

Next, a saturation distance $D_{SAT}(x, y)$ is calculated using formula 8. The saturation distance $D_{SAT}(x, y)$ is a relative value of saturation of the decision image data J(x, y) using saturation $S_{ref}$ of the blood sample data as reference.

$$D_{SAT}(x, y)=S_{corr.}(x, y)-S_{ref}$$ (Formula 8)

[Determination of Saturation Correlation Value SCV: S76]

Next, a saturation correlation value SCV(x, y) is determined based on the saturation distance $D_{SAT}(x, y)$ (S76). The saturation correlation value SCV(x, y) is also a parameter having strong correlation with the severity degree of the inflammation part. FIG. 10(b) is a graph showing a relationship between the saturation distance $D_{SAT}(x, y)$ and the saturation correlation value SCV. The saturation distance $D_{SAT}(x, y)$ has strong correlation with the severity degree of the inflammation part in a negative range in which the saturation distance $D_{SAT}$ has a value equal to or greater than a predetermined value (hereinafter, referred to as a saturation approximation range $R_{22}$), while the saturation distance $D_{SAT}$ has little correlation in a negative range and the saturation distance $D_{SAT}$ has a value equal to or less than the predetermined value. Further, in a range in which the saturation distance $D_{SAT}$ is zero or greater, that is, in a range where the saturation of the lesion pixel is equal to or greater than the saturation Sref of the blood sample data (hereinafter, referred to as saturation coincidence range $R_{21}$), it is considered that the severity degree is quite high. Therefore, the saturation correlation value SCV(x, y) according to the present embodiment is configured such that the saturation correlation value SDV(x, y) is set to have the maximum value of 1.0 within the saturation coincidence range $R_{21}$, set to have the minimum value of 0.0 within the non-saturation approximation range $R_{23}$, and set to linearly increase within the saturation approximation range $R_{22}$. It is noted that the saturation correlation value SCV(x, y) is also a normalized value which has the minimum value of 0.0 and the maximum value of 1.0.

The relationship between the saturation distance $D_{SAT}$ and the saturation correlation value shown in FIG. 10(b) is stored in the memory 229 in form of a saturation correlation value table SCT. By referring to the saturation correlation table SCT, a saturation correlation value SCV(x, y) corresponding to a saturation distance $D_{SAT}(x, y)$ can be obtained.

[Calculation of Correlation Value: S77]

Next, by multiplying the hue correlation value HCV(x, y) with the saturation correlation value SCV(x, y), a correlation value CV(x, y) between the color of a lesion pixel (x, y) and the color of blood. It is noted that the correlation value CV(x, y) is a normalized value of which the minimum value is 0.0 and the maximum value is 1.0. Further, the correlation value CV(x, y) is divided into eleven steps with a pitch of 0.1 point.

[Update of Score Sc: S78]

Since the correlation value CV(x, y) serves as an appropriate index of severity degree of the inflammation, the value of the score Sc(x, y) in the score table ST is rewritten with the correlation value CV(x, y) (S78).

[Updating of Score Sc: S79]

When a pixel (x, y) is not the lesion pixel (S71: NO), the above-described calculation of the correlation value CV(x, y) is not executed, and the value of the score Sc(x, y) in the score table ST is rewritten with "0" (S79). According to this configuration, scores Sc(x, y) can be given to all the pixels (x, y) with a smaller amount of calculations.

In process S80, it is judged whether the processing has been completed for all the pixels (x, y). Until processing has been completed for all the pixels (x, y), above-described processes S71-S80 are repeated.

[Marking Process: S8]

When the score calculating process S7 has completed, a marking process S8 is executed subsequently by the marking processing part 226. The marking process S8 is a process to apply marks to an image area of the normal observation image NP so that the lesion part can be recognized easily. Specifically, according to the marking process S8 of the embodiment, marks of which size correspond to a severity degree in the image area (e.g., a mark 330 or a mark "x" in FIG. 16) are applied to the image area in which the lesion parts distribute.

Figure 11:
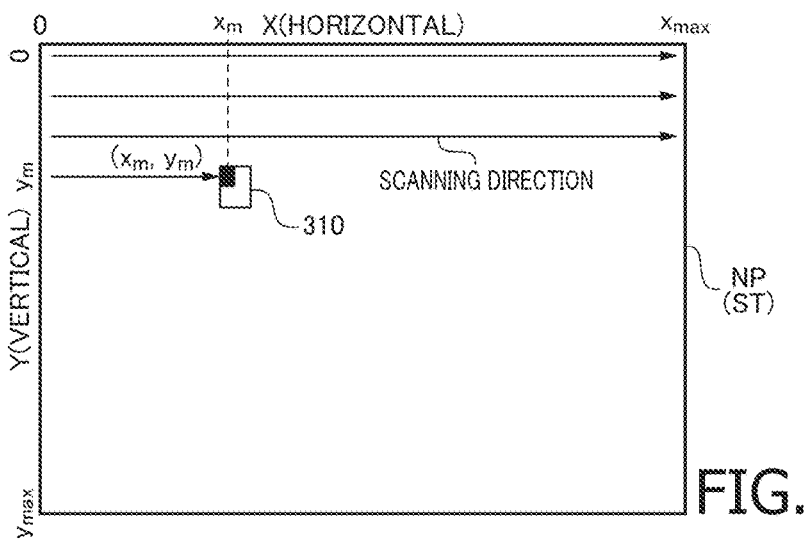
FIG. 11 is a figure showing a marking process (scanning of a mask).

FIG. 11 illustrates a procedure of the marking process S8 (i.e., a scanning of a mask 310). According to the marking process S9 of the present embodiment, a mask 310 which is an image of a predetermined size is set in the normal observation image NP (and in the score table ST), and the marks 330 are applied to the image within the mask 310 based on the scores Sc of the pixels 311 (FIG. 12) with sequentially moving the mask 310.

[Configuration of Mask]

Figure 12:
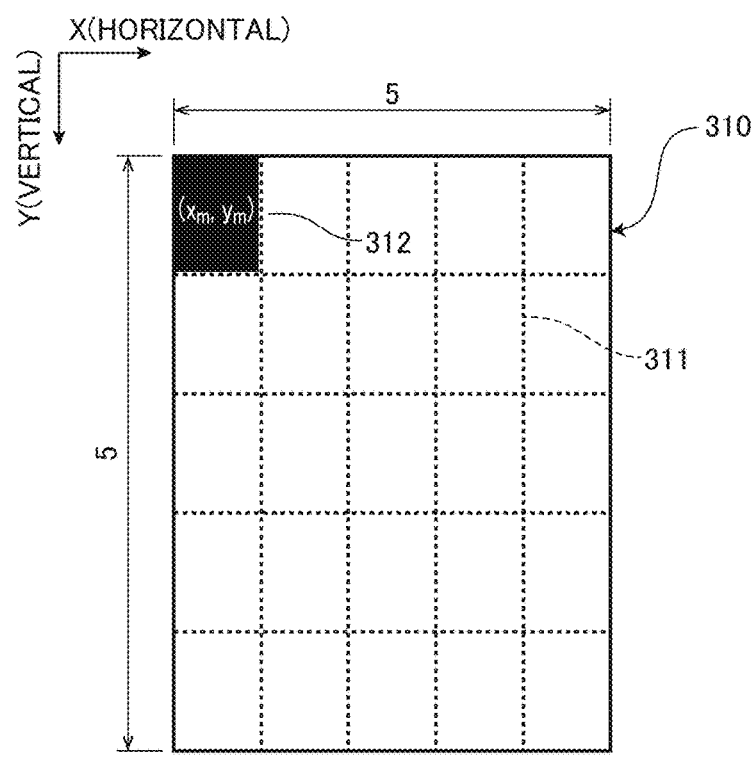
FIG. 12 is a figure showing a configuration of the mask.

According to the embodiment, a size of the mask 310 (and, a size of the mark 330 which is determined based on the size of the mask) varies depending on the scores Sc of the pixels 311 within the mask 310. FIG. 12 shows the mask 310 having a predetermined initial size. According to the embodiment, the initial size of the mask 310 is 5×5 (i.e., the number of pixels in the horizontal direction X the number of pixels in the vertical direction). The initial size of the mask 310 is set in accordance with, for example, visibility of the mark 330 applied to the image within the mask 310 (e.g., complexity of the shape of the mask 330, the number of the display screen of the monitor 910, and the like). Specifically, the initial size of the mask 310 is set to be the minimum size within the limit that the marks 330 can be displayed as many as possible to retain the good visibility of the marks 330.

The mask size is determined based on the score Sc, referring to the mask table MT stored in the memory 229. Table 1 is an example of the mask table MT used in the embodiment. According to the embodiment, the initial size (5×5) is the lower limit of the mask size, and the mask size increases proportional to the score Sc.

TABLE 1

| | SCORE Sc | | | | | | | | | | |
|---|---|---|---|---|---|---|---|---|---|---|---|
| | 0.0 | 0.1 | 0.2 | 0.3 | 0.4 | 0.5 | 0.6 | 0.7 | 0.8 | 0.9 | 1.0 |
| Mask size | — | 5 × 5 | 6 × 6 | 7 × 7 | 8 × 8 | 9 × 9 | 10 × 10 | 11 × 11 | 12 × 12 | 13 × 13 | 14 × 14 |

As shown in FIG. 12, among the multiple pixels 311 constituting the mask 310, the upper left one (i.e., a pixel of which x and y coordinates are minimum) is referred to a reference point 312. The position of the reference point 312 ($x_m$, $y_m$) is defined as the location of the mask 310. It is noted that the any pixel within the mask 310 may be set to the reference point 312.

[Scanning of Reference Point: S81]

Figure 13:
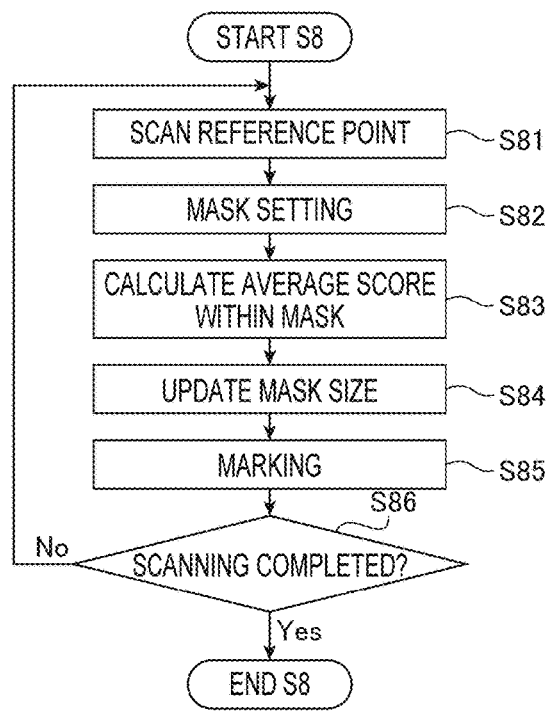
FIG. 13 is a flowchart illustrating a procedure of the marking process.

FIG. 13 is a flowchart illustrating a procedure of the marking process S8. In the marking process S8, firstly, the normal observation image data N (original image) stored in the storage area Pn the image memory 227 is copied and stored in the storage area Pm as an initial value of the marking image data M. Further, the score table ST is retrieved from the memory 229, and scanning of the reference point 312 is executed on the score table ST (S81). According to the embodiment, the reference point 312 is sequentially scanned from the uppermost line (y=0) of the score table ST to the lowermost line (y=$y_{max}$) (FIG. 11). Further, the reference point 312 is scanned from the left end (x=0) to the right end (x=$x_{max}$) in each line.

The marking processing part 226 searches for a position (x, y) satisfying both of conditions a and b below with scanning the reference point 312 on the score table ST.

Condition a: to be a lesion pixel [the score Sc(x, y) is 0.1 or more]

Condition b: the mask 310 does not overlap the mark 330 already applied (more accurately, the mask 310 when the mark is applied)

[Mask Setting: S82]

Reaching a position (x, y) where both the conditions a and b are satisfied, a mask having the initial size (5×5) is set at the position (S82).

[Calculation of In-Mask Average Score: S83]

Next, an average score $Sc_{Avg}$ which is an additive average of the scores Sc(x, y) of the pixels within the mask is calculated (S83). Incidentally, the average score $Sc_{Avg}$ has a normalize value of which the minimum value is 0.0 and the maximum value is 1.0. it is noted that the average score $Sc_{Avg}$ may be replaced with another numerical value representing the in-mask scores Sc(x, y) (e.g., a weighted average, a median value, a most frequent value, a root-mean-square value, or the like).

[Mask Size Update: S84]

Next, referring to the mask table MT stored in the memory 229, the mask size corresponding to the average score $Sc_{Avg}$ is retrieved. Then, the size of the mask 310 is updated to be the mask size as retrieved (the mask 310 is re-set) (S84).

[Marking S85]

Next, with respect the marking image data M, the mark 330 is applied to inscribe in edges of the mask 310 after re-setting (S85).

In process S86, it is judged whether scanning has reached to the end of the score table ST. Until all the sores Sc(x, y) have been scanned, the above processes S81-S86 are repeated.

[Concrete Example of Marking Process: FIGS. 14-20]

Next, referring to. FIGS. 14-20, a concrete example of the marking process S8 will be described. In the normal observation image data N (score table ST) shown in FIGS. 14-20, an image 320 of a lesion part including multiple lesion pixels 321.

Figure 14:
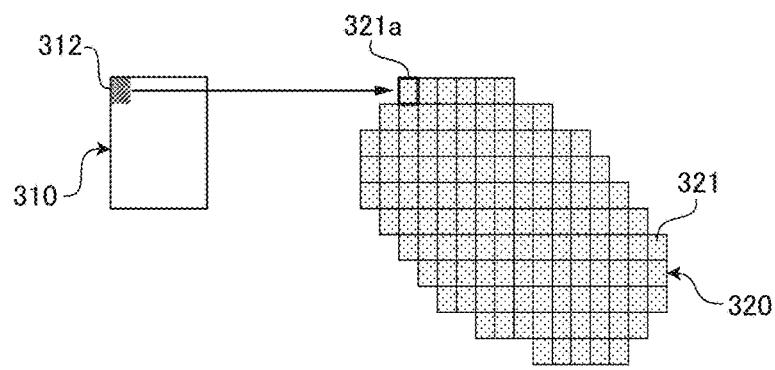
FIG. 14 is a figure illustrating a concrete example of the marking process.

As shown in FIG. 14, as the reference point 312 of the mask 310 is scanned, on the score table ST, from the upper left for each line sequentially (S81), a lesion pixel 321a is firstly detected.

In order that the lesion pixel 321a satisfies the above conditions a and b, the mask 310a having the initial size (5×5) (i.e., a frame of broken lines in FIG. 15) is set with the lesion pixel 321a being regarded as the reference point.

Next, an average value (i.e., an average score $Sc_{Avg}$) of the scores Sc(x, y) within the mask 310a is calculated (S83).

Figure 15:
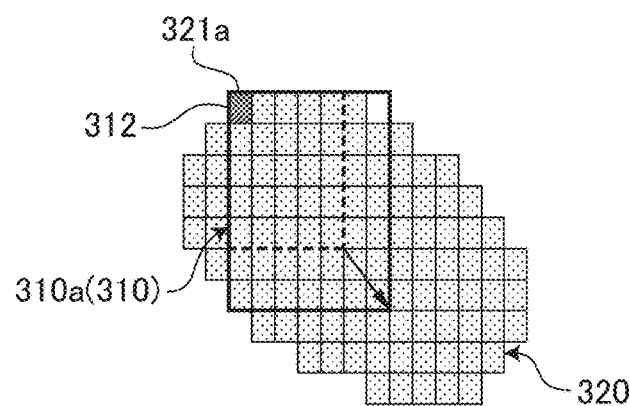
FIG. 15 is a figure illustrating a concrete example of the marking process.

If the calculation result of the average score ScAvg is, for example, 0.3, the mask size 7×7 corresponding the value of the average score ScAvg is obtained from the mask table MT (Table 1), and the size of the mask 310a is changed to 7×7 (i.e., a frame indicated by solid line in FIG. 15).

Then, with respect to the marking image MP, marks "x" 330 are applied so as to inscribe in the edges of the mask 310a (S85). It is noted that "x" is used as the mark 330 according to the embodiment, any marks (including letters, numbers, symbols, pictures, patterns and the like, except for ones covering the whole mask 310) can be used.

Figure 16:
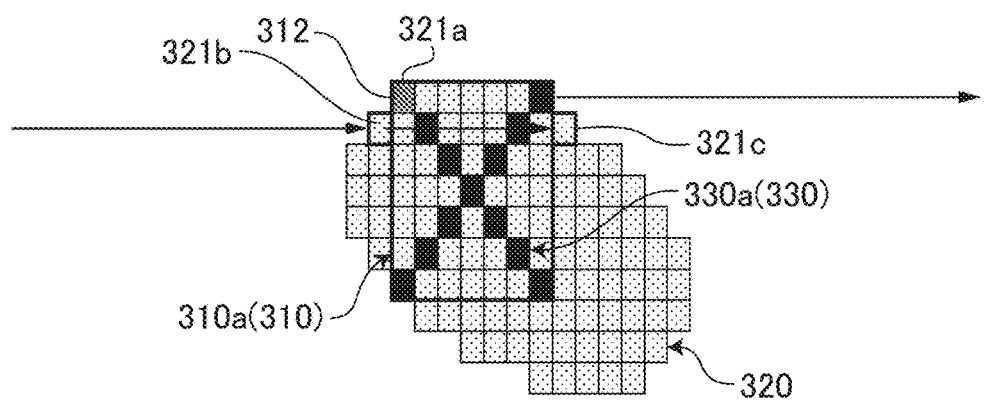
FIG. 16 is a figure illustrating a concrete example of the marking process.
Figure 17:
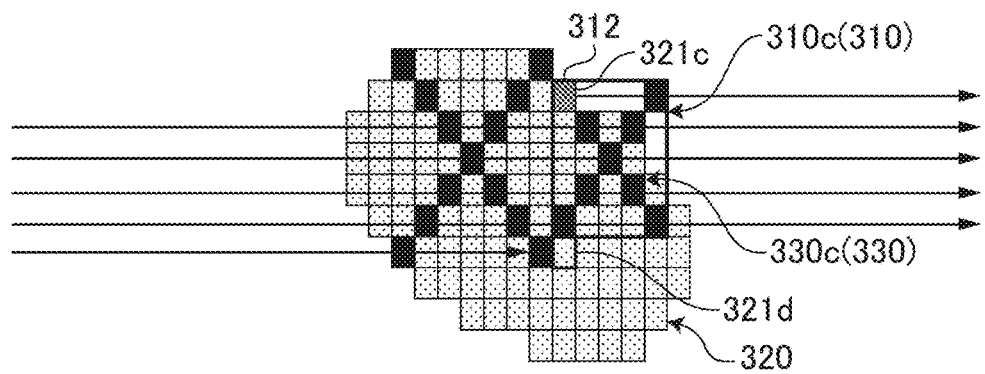
FIG. 17 is a figure illustrating a concrete example of the marking process.
Figure 18:
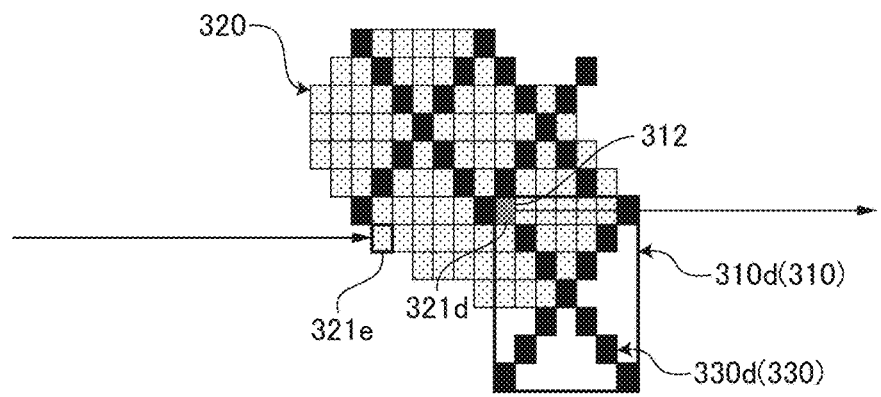
FIG. 18 is a figure illustrating a concrete example of the marking process.
Figure 19:
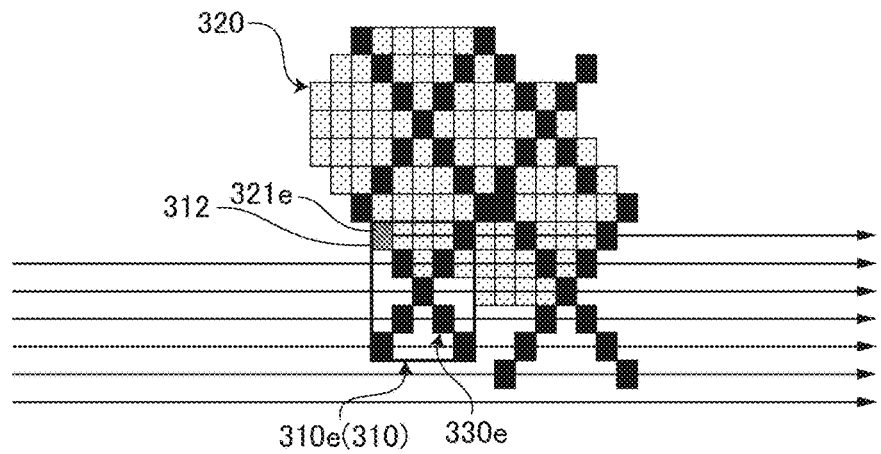
FIG. 19 is a figure illustrating a concrete example of the marking process.

Next, the reference point 312 is scanned again (FIG. 16). Inside the mask 310a previously set does not satisfy above condition b, and scanning is skipped. Further, one aline of the lesion pixel 321a, there is no lesion pixel 321 satisfying both the conditions a and b, scanning is executed below by one line, and the lesion pixel 321b is detected. However, if the mask 310 is set starting from the lesion pixel 321b, it interferes with the previously set mask 310a. Therefore, the scanning is continued without setting the mask 310 at the lesion pixel 321b. Then, immediately after skipping the previously set mask 310a, the lesion pixel 321c is detected.

Both the above conditions a and b are satisfied in the lesion pixel 321c, a mask 310c (FIG. 17) having the initial size (5×5) starting from the lesion pixel 321c is set. If the average score ScAvg within the mask 310c is, for example, 0.1, the corresponding mask size is the initial size (5×5) and unchanged, the mask size is not updated, and the mark "x" 330c is applied so as to inscribe the edges of the mask 310c.

Figure 20:
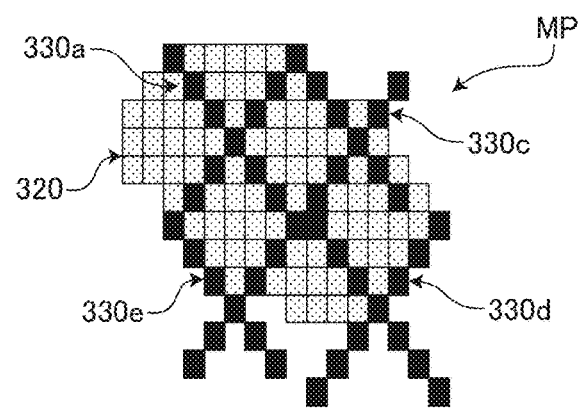
FIG. 20 is a figure illustrating a concrete example of the marking process.

Thereafter, processes S81-S86 are repeated similarly, "x" mark 330d is applied to the mask 310d which is set from the lesion pixel 321d (FIG. 18), further, "x" mark 330e is applied to a mask 310e which is set from the lesion pixel 321e (FIG. 19), and then scanning of the normal observation image data N (i.e., score table ST) is completed. As a result, a marking image MP on which a position of the image of the lesion part, and marks 330a, 330c, 330d and 330e indicating distribution of the severity degree thereof are applied is obtained (FIG. 20). The marking image data M as generated is stored in the storage area Pm of the image memory 227.

[Generating Process—Outputting Process of Display Screen: S9-S10]

When the marking process S8 has completed, a display screen generating process S9 is executed subsequently. The display screen generating process S9 is to generate display screen data to display a screen on the monitor 900 using various pieces of image data stored in the image memory 227, and is executed by the display screen generating part 228 of the image processing circuit 220. The display screen generating part 228 is capable of generating plurality of kinds of display image data in accordance with control of the system controller 202. To the display screen data as generated, processing such as a gamma compensation is applied by the output circuit 220b, and then converted into a video signal having a predetermined video format and output to the monitor 900 (outputting process S10).

Figure 21:
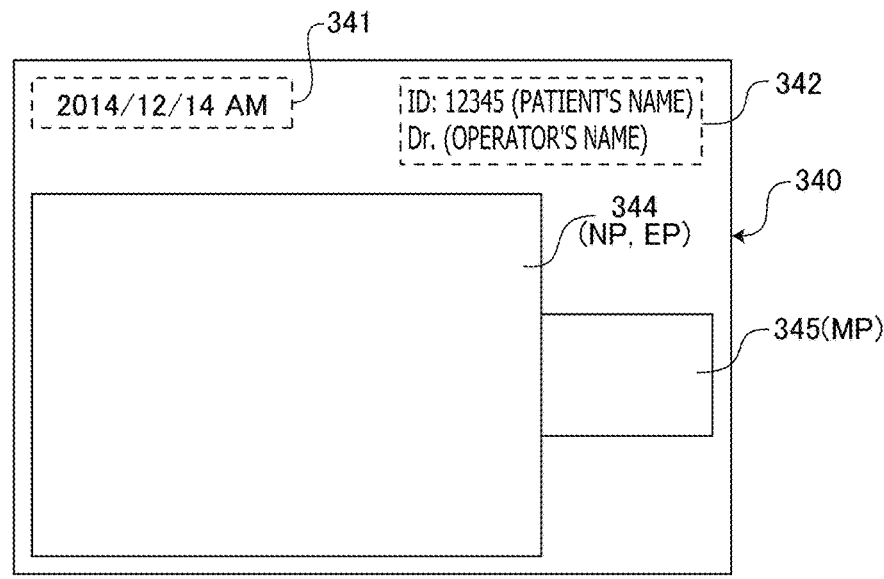
FIG. 21 shows an example of a display screen.

FIG. 21 shows an example of a display screen generated by the display screen generating process S9, and is an analysis mode observation screen 340 which is displayed when the endoscopic observation in the image analyzing mode is carried out. The analysis mode observation screen 340 includes a date/time display area 341 in which photographed date and time are displayed, a basic information display area 342 in which basic information regarding the inspection (e.g., a medical card number, a patient's name, an operator's name), a normal image display area 344 in which the normal observation image NP (or the tone-enhanced image EP) is displayed, and an analysis image display area 345 in which the marking image MP (an observation image after the marking process S8) is displayed.

In the display screen generating process S9, the display image generating part 228 retrieves the normal observation image data N (or, retrieves the tone-enhanced image data E from storage area group Pe), and displays the normal observation image NP (or, the tone-enhanced image EP) on the normal image display area 344. Further, the display image generating part 228 retrieves the marking image data M from a storage area group Pm, and displays the marking image MP on the analysis image display area 345. Further, in the date/time display area 341 and the basic information display area 342, information supplied from the system controller 202 is displayed.

The operator carries out the endoscopic observation with watching the analysis mode observation screen 340. Specifically, the operator carries out the endoscopic observation with watching the normal observation image NP (or the tone-enhanced image EP) displayed in the normal image display area 344, with reference to the marking image MP displayed in the analysis image display area 345. By carefully observing particularly carefully a where a marking is applied in the marking image MP, an accurate medical examination can be carried out without overlooking a lesion part.

According to the present embodiment, since the mark 330, through which the normal observation image NP on the background can be seen, is applied, the endoscopic observation and diagnosis can be carried out with only viewing the marking image MP. Accordingly, it is configured, for example, that the analysis mode observation screen 340 including a large analysis image display area 345 and not including the normal image display area 344 is generated.

After completion of the display screen generating process S9 and outputting process S10, it is judged whether the endoscopic observation is to be continued (S11). Until a user operation to instruct end of the endoscopic observation or stoppage of operating the electronic endoscope apparatus 1 is carried out (S11: NO), the processes S1-S11 are repeated.

The foregoing is an explanation of the first embodiment of the present invention. According to the configuration of the first embodiment of the present invention, since the mark 330 indicating the location of the lesion part and the severity degree thereof is applied on the image 320 of the lesion part in the marking image MP, even an inexperienced operator of the endoscopic observation can carry out accurate diagnosis with use of the endoscopic image easily, without overlooking lesion parts or mistaking the severity degree. Further, on the marking image MP, the mark 330 which does not completely cover the background (i.e., the image 320 of the lesion part) but allows a part of the background to be seen through a space (i.e., has a transparency). With this configuration, since the shape or texture of the lesion part can be grasped, more efficient and accurate diagnosis is enabled.

Incidentally, the first embodiment described above, the marking image MP is generated by applying the mark 330 to the normal observation image NP. However, the marking image MP may be generated by applying the mark 330 to the tone-enhanced image EP or a processed image of the normal observation image NP.

<First Modification of First Embodiment>

Next, some modifications of the first embodiment of the present invention described above will be explained.

Figure 22:
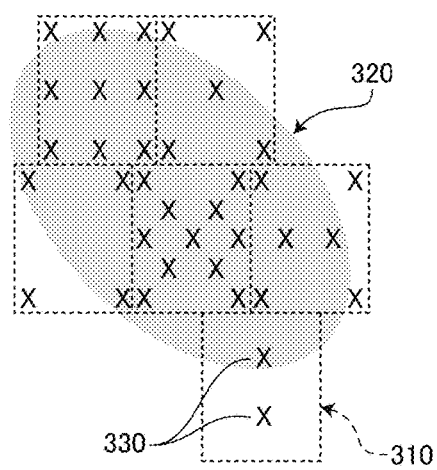
FIG. 22 shows a marking image according to a first modification of the first embodiment of the present invention.

FIG. 22 is a marking image MP of a first modification of the first embodiment of the present invention. According to the above-described first embodiment, in the mask size updating process S84, there is employed a configuration in which the mask size is updated in accordance with the average score $Sc_{Avg}$ within the mask 310 and the severity degree is shown by the size of the mark 330. Incidentally, according to the first modification, not the mask size bu the number of the marks 330 applied to inside the mask 310 is set in accordance with the average score ScAvg within the mask 310. According to the present modification, the severity degree is expressed by the density of the marks 330.

Incidentally, according to the present modification, instead of the mask table MT (Table 1) in the first embodiment, a mark number table storing a relationship between the average score ScAvg within the mask 330 and the number of the marks to be applied within the mask is used. An example of the mark number table is shown in FIG. 2.

TABLE 2

| | Score Sc | | | | | | | | | | |
|---|---|---|---|---|---|---|---|---|---|---|---|
| | 0.0 | 0.1 | 0.2 | 0.3 | 0.4 | 0.5 | 0.6 | 0.7 | 0.8 | 0.9 | 1.0 |
| The number of Marks | 0 | 1 | 2 | 3 | 4 | 5 | 6 | 7 | 8 | 9 | 10 |

<Second Modification of First Embodiment>

Figure 23:
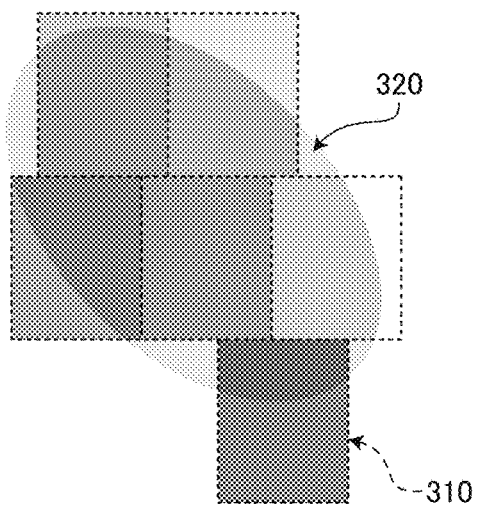
FIG. 23 shows a marking image according to a second modification of the first embodiment of the present invention.

FIG. 23 shows a marking image MP according to a second modification of the first embodiment of the present invention. In the first embodiment described above, marking is done by applying characters and symbols within the mask 310. According to the present modification, locations and severity degrees of the lesion parts are displayed by varying the colors within the masks 310, with respect to the normal observation image NP, depending on the average scores $Sc_{Avg}$ within the masks 310 (in other words, by applying color marks).

Further, according to the present modification, inside of a mask is filled with a single color (transparency is 0%) with respect to the normal observation image NP, but a color given a predetermined transparency (e.g., the transparency of 80%) is applied onto the normal observation image NP. Therefore, similar to the first embodiment, information regarding the image of the lesion part is remained in the marking image MP, and, in comparison with a conventional method in which the lesion part is fully filled with a predetermined color, it becomes possible to carry out the accurate diagnosis.

Further, according to the present modification, since it is unnecessary to recognize the shape of the symbols applied to the lesion part, the size of the mask can be set to 1×1 (or, processing is executed for each pixel without using the mask).

Incidentally, according to the present modification, instead of the mask table MT (Table 1) in the first embodiment, a display color table storing a relationship between the scores Sc(x, y) of respective pixels (x, y) and the colors Col(x, y) to be applied to the respective pixels (x, y) is used. An example of the display color table (24-bit color) is shown in Table 3. It is noted that, for the pixels (x, y), of which the values of the scores Sc(x, y) are zero (i.e., the normal tissues), null values are assigned. Accordingly, the pixels of the normal tissues are not colored. It is noted that designation of a color to be assigned to each pixel (x, y) need not be limited to the designation by RGB, but another color expression (e.g., hue and/or saturation) may be used for designation.

TABLE 3

| | SCORE Sc | | | | | | | | | | |
|---|---|---|---|---|---|---|---|---|---|---|---|
| | 0.0 | 0.1 | 0.2 | 0.3 | 0.4 | 0.5 | 0.6 | 0.7 | 0.8 | 0.9 | 1.0 |
| R value | Null | 0 | 0 | 0 | 0 | 0 | 0 | 255 | 255 | 255 | 128 |
| G value | Null | 0 | 0 | 128 | 128 | 255 | 255 | 255 | 0 | 0 | 128 |
| B value | Null | 255 | 128 | 128 | 0 | 0 | 255 | 0 | 0 | 255 | 0 |

<Second Embodiment>

Figure 24:
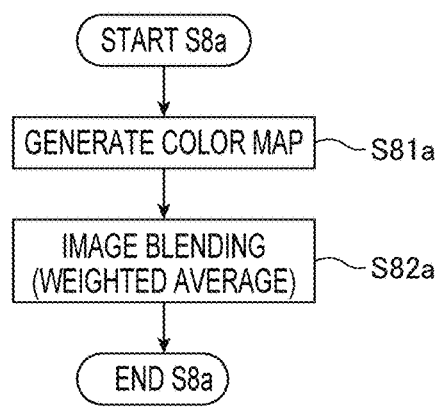
FIG. 24 is a flowchart showing a procedure of the marking process according to the second embodiment of the present invention.

Next, a second embodiment of the present invention will be described:

FIG. 24 is a flowchart showing a procedure of a marking process S8a of the second embodiment. The marking process S8a of the present embodiment is executed instead of the marking process S8 of the first embodiment. Further, the marking process S8a of the present invention executed with respect to all the pixels (x, y) constituting the normal observation image data N sequentially.

In the electronic endoscope apparatus 1 according to the present embodiment, the display color table (Table 3) is stored in the memory 229 as in the second modification of the first embodiment described above. Further, in the image memory 227 of the present embodiment, in addition to the storage areas Pn, Pe and Pm, a storage area PC configured to store the color map image data CM (i.e., image data representing the color map image CMP) generated in the marking process S8a (see FIG. 3(b)) is allocated (see FIG. 3(b)).

[Color Map Image Data Generation: S81a]

In the marking process S8a, firstly, the display color table stored in the memory 229 is referred to, and the colors Col(x, y) applied to respective pixels are determined based on the scores Sc(x, y). It is noted that the colors Col(x, y) of the pixels other than the lesion pixels are set to be colorless and transparent (i.e., null value). Thereafter, the color map image data CM having the colors Col(x, y) of respective pixels (x, y) is generated, and stored in the storage area Pc of the memory 229 (S81a).

[Image Blending Process: S82a]

Next an image blending process S82a to cause the color maop image CMP to have transparency and to be overlaid on the normal observation image NP is executed. Specifically, the image blending process S82a is a process of weighted-averaging the normal observation image data N and the color map image data CM. By calculating the weighted average, transparency can be applied to the color map image CMP, which can be overlaid on the normal observation image NP. It is noted that the weight of the normal observation image data N in the weighted averaging is determined based on the transparence of the color map image CMP which is determined in advance. The marking image data M generated by the image blending process S82a is stored in the storage area Pm of the image memory 227, and the marking process S8a is terminated. Incidentally, the weighed averaging is applied only to the lesion pixels (score Sc(x, y)>0), and, with respect to the pixels (x, y) of a healthy part (scores Sc(x, y)=0), the pixel values N(x, y) of the normal observation image data N are used as they are as pixel values M(x, y) of the marking image data M.

Figure 25:
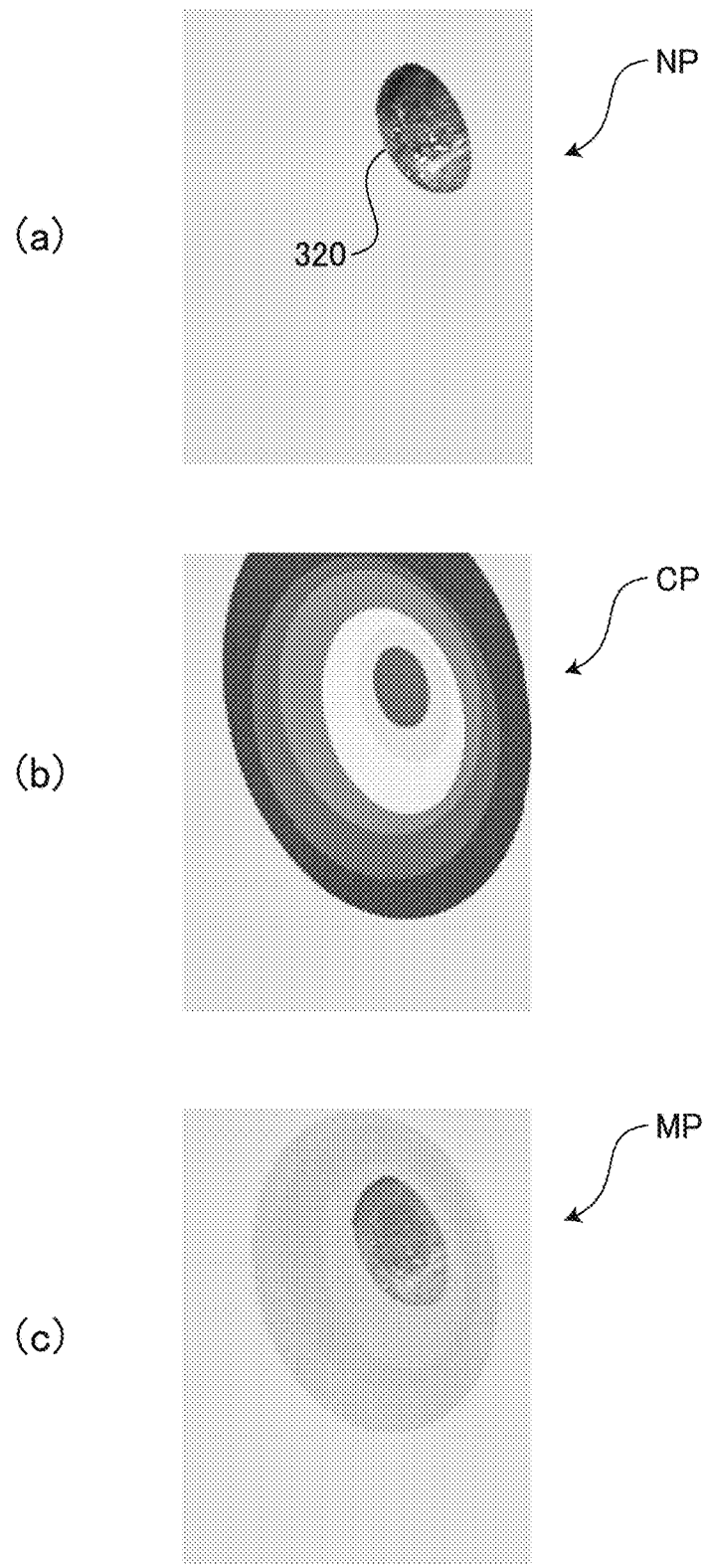
FIG. 25 is a figure illustrating effects of an image blending process.

Here, referring to FIG. 25, effects of the image blending process S82a will be explained.

FIG. 25(a) shows a normal observation image NP including the image 320 of the lesion part.

FIG. 25(b) shows a normal observation image NP with a color map image CMP being overlaid as it is (transparency is 0%).

FIG. 25(c) shows a marking image MP generated in the image blending process S82a according to the present embodiment.

As is apparent by comparing (b) and (c), from the marking image MP generated in the image blending process S82a, parts suspected to he lesion parts or assumed severity degree can be visibly recognized easily with use of the color map. Further, since the color map has transparency, shape and texture of the lesion part can be grasped to a certain extent from the marking image MP, the medical examination can be carried out easier.

<Third Embodiment>

Next, a third embodiment according to the present invention will be explained. According to the present embodiment. by overlaying contour lines of the scores Sc(x, y) on the normal observation image NP, locations of lesion parts and/or distribution of the severity degrees are displayed with good visibility.

Figure 26:
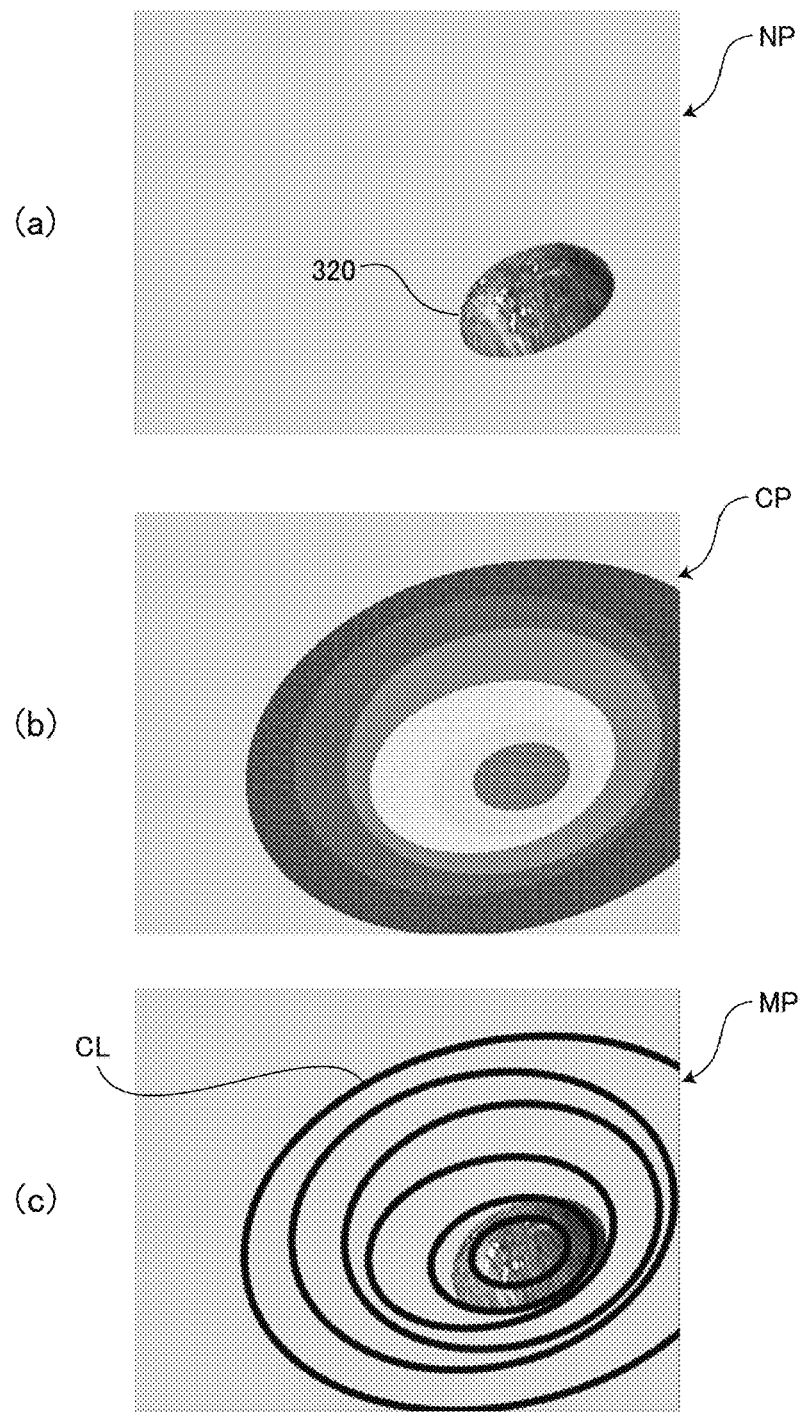
FIG. 26 is a figure illustrating a method of generating contour lines according to a third embodiment of the present invention.

FIG. 26 shows a generation process of the contour lines CL according to the third embodiment. According to the present embodiment, firstly, a color map image CMP as shown in FIG. 26(b) is generated based on the score table ST generated from the normal observation image NP including the imag 320 of the lesion part indicated in FIG. 26y(a) and referring to the color map table (Table 3). Then, contour liens for the color map image CMP are generated by applying processes such as vector differential operation and the like to the color map image data CM. Then, by overlaying the contour lines thus generated on the normal observation image NP, the marking image MP according to the present embodiment as shown in FIG. 26(c) is generated.

The foregoing is the description of the illustrative embodiments. Embodiments of the present invention are not limited to those described above, and various modifications can be made within technical philosophy of the present invention. For example, appropriate combinations of illustratively indicated embodiments in the specification are also included in embodiments of the present invention.

In the above-described embodiment, image analysis such as determination of lesions and the like is executed in the HIS space. Instead of the HIS space, the image analysis may be executed in an HSV(HSB) space based on the hue, saturation and value or brightness. Further, the image analysis may be executed in another type of color space having one coordinate representing intensity of brightness, and two coordinates representing color qualities (e.g., hue, saturation, chromaticity), such as a CIE 1976 L*a*b* color space, a YCbCr color space and the like.

Incidentally, the TE process S3 is executed in the RGB space in the above-described embodiment, it may be configured such that the TE process S3 is executed on the HIS space after the color space converting process S5.

Further, instead of the TE process S3 (tone enhancing process), another type of image enhancing process such as a contrast enhancing process (e.g., a histogram equalizing method to enhance the contrast by widening a distributing width of the histogram), an image sharpening process with use of an unsharp mask filter, and the like may be used.

The above-described embodiments show examples of applying the present invention to the endoscopic inspection of the inflammatory bowel disease, and the present can also be applied to the endoscopic inspections for another disease as a matter of course.

The above-described embodiments show examples of evaluating the severity degree of only one kind of lesion (inflammation) based on the observing image, and applying marks corresponding to the severity degree on a suitable portion of the observation image. It is noted that a configuration in which severity degrees of multiple types of lesions (e.g., inflammation and ulcer which are characteristic lesions in the inflammatory bowel disease) are determined respectively, and marks corresponding to the severity degrees are applied to respective portions of the observation image. Further, in such a case, displaying modes (e.g., types and/or colors of symbols) may be differentiated for respective lesion types.

In the above-described embodiments, marks are applied to lesion parts. In contrast, it is configured such that the marks are applied to healthy parts. It may be further configured such that different marks are applied to lesion parts and healthy parts, respectively.

The above-described embodiments are configured to display the severity degree of the lesion part with use of one of the symbol, contour line and color. It is noted that two or more of the above three displaying modes may be used in combination to display the severity degree of the lesion part. Further, two or more of type, size and color of the symbol may be used in combination to display the severity degree. Further, one of or a combination of more than one of the type (solid line, broken line, chained line, wave line and the like), thickness and color, may be used to display the severity degree.

The above-described embodiments show examples in which the present invention is applied to the electronic endoscope apparatus which is one form of a digital camera, and the present invention can also be applied to a system using another type of digital cameras (e.g., a digital still camera or a digital video camera). For example, when the present invention is applied to the digital still camera, a diagnosis support for examination of the lesion part of body surface tissues or a diagnosis support for examination of brain tissues when a craniotomy procedure is carried out.

What is claimed is:

1. An image processing apparatus, comprising:
   an imager configured to obtain color image data representing a color image of biological tissue;
   a processor; and
   a memory storing instructions that, when executed by the processor, cause the processor to perform operations including:
   determining whether each pixel of the color image is of a lesion based on the color image data;
   setting a predetermined imaging area including a pixel determined by the determining to be a pixel capturing a portion of the lesion; and
   applying a mark indicating a position of the portion of the lesion on the color image based on a result of the determining, the applying including overlaying the mark on a part of the set predetermined imaging area such that at least a part of the portion of the lesion in the set predetermined imaging area is not hidden by the mark,
   wherein the mark is configured such that the color image at a background of the mark can be seen.

2. The image processing apparatus according to claim 1, wherein the determining comprises generating a score table including, as an element, a score representing a degree of severity of the lesion of the biological tissue per each pixel of the color image, and wherein the applying includes applying the mark indicative of a position and the degree of severity of the lesion on the color image based on the score table.

3. The image processing apparatus according to claim 2, wherein the applying includes:
setting a mask which is a process target area within the color image;
calculating a representative value of the score within the mask; and
applying the mark to the mask based on the representative value.

4. The image processing apparatus according to claim 3, wherein the applying includes:
setting the mask having a predetermined initial size;
calculating the representative value regarding the mask having the predetermined initial size;
changing the size of the mask in accordance with the representative value; and
applying the mark such that the mark inscribes in the mark of which size has been changed.

5. The image processing apparatus according to claim 4, wherein the initial size is a minimum size of the mask.

6. The image processing apparatus according to claim 3, wherein the applying includes applying a corresponding number, that corresponds to the representative value, of the marks in the mask.

7. The image processing apparatus according to claim 3, wherein the applying includes applying the marks on the color image causing the mask to scan within the color image.

8. The image processing apparatus according to claim 7, wherein the applying includes setting the mask so as not to overlap another mask having been set.

9. The image processing apparatus according to claim 3, where the representative value is one of an arithmetic mean value, a weighted average value, a median value, a maximum frequency value, and a root-mean-square value.

10. The image processing apparatus according to claim 2, wherein the generating comprises:
converting a color space of the color image data to another color space having one coordinate indicating intensity or brightness and two coordinates indicating color quality; and
calculating the score per each pixel based on a quality of color of each pixel of the color image data.

11. The image processing apparatus according to claim 10, wherein the generating further comprises executing a color enhancement processing to enhance contrast of the color quality at a boundary area within a pixel range value which is significant in the lesion, and
wherein the calculating the score includes calculating the score of each pixel based on the pixel values after the color enhancement processing has been executed.

12. The image processing apparatus according to claim 10, wherein the calculating the score includes calculating the score of each pixel based on a distance to a reference point in a hue-saturation space or a chromaticity space.

13. The image processing apparatus according to claim 12, wherein:
the lesion is an area of inflammation; and
the reference point is a blood color.

14. The image processing apparatus according to claim 1, wherein the mark is a symbolic character.

15. The image processing apparatus according to claim 1, wherein the mark is a color having transparency.

16. The image processing apparatus according to claim 2, wherein the mark includes contour lines degree according to the degree of severity of the lesion.

17. The image processing apparatus according to claim 1, wherein the color image is an image taken by an electronic endoscope.

18. An image processing apparatus, comprising:
an imager configured to obtain color image data representing a color image of biological tissue;
a processor; and
a memory storing instructions that, when executed by the processor, cause the processor to perform operations including:
determining whether each pixel of the color image is of a lesion based on the color image data, and generating a score table including, as an element, a score representing a degree of severity of the lesion of the biological tissue per each pixel of the color image; and
applying a mark indicating a position and the degree of severity of the lesion on the color image based on the score table, the applying including:
setting a mask which is a process target area within the color image,
calculating a representative value of the score within the mask, and
applying the mark to the mask based on the representative value,
wherein the mark is configured such that the color image at a background of the mark can be seen, and
wherein the representative value is one of an arithmetic mean value, a weighted average value, a median value, a maximum frequency value, and a root-mean-square value.

* * * * *